(12) United States Patent
Teague et al.

(10) Patent No.: US 8,388,630 B2
(45) Date of Patent: Mar. 5, 2013

(54) MEDICAL RETRIEVAL DEVICES AND METHODS

(75) Inventors: James A. Teague, Spencer, IN (US); Joseph Desmond, Bloomington, IN (US); Timothy Ward, Springville, IN (US); James Riley, Bloomington, IN (US); Ryan Ludwig, Bloomington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 697 days.

(21) Appl. No.: 10/942,105

(22) Filed: Sep. 16, 2004

(65) Prior Publication Data

US 2005/0119668 A1 Jun. 2, 2005

Related U.S. Application Data

(60) Provisional application No. 60/504,243, filed on Sep. 18, 2003.

(51) Int. Cl.
*A61B 17/221* (2006.01)

(52) U.S. Cl. ....................................................... 606/127

(58) Field of Classification Search .................. 606/108, 606/110, 113, 114, 127, 190, 209, 106, 194, 606/198, 200, 159, 12; 604/523–527, 104–107
See application file for complete search history.

(56) References Cited

U.S. PATENT DOCUMENTS

| | | | |
|---|---|---|---|
| 4,174,715 A | 11/1979 | Hasson | |
| 4,548,206 A * | 10/1985 | Osborne | 600/585 |
| 4,576,772 A * | 3/1986 | Carpenter | 264/154 |
| 4,811,735 A | 3/1989 | Nash et al. | |
| 5,192,286 A * | 3/1993 | Phan et al. | 606/127 |
| 5,520,697 A * | 5/1996 | Lindenberg et al. | 606/108 |
| 5,531,719 A * | 7/1996 | Takahashi | 604/525 |
| 5,562,678 A * | 10/1996 | Booker | 606/113 |
| 5,752,961 A * | 5/1998 | Hill | 606/113 |
| 5,792,145 A * | 8/1998 | Bates et al. | 606/127 |
| 5,807,241 A * | 9/1998 | Heimberger | 600/142 |
| 5,944,728 A | 8/1999 | Bates et al. | |
| 6,099,534 A * | 8/2000 | Bates et al. | 606/127 |
| 6,183,482 B1 * | 2/2001 | Bates et al. | 606/127 |
| 6,224,612 B1 * | 5/2001 | Bates et al. | 606/114 |
| 6,280,451 B1 * | 8/2001 | Bates et al. | 606/127 |
| 6,348,056 B1 * | 2/2002 | Bates et al. | 606/114 |
| 6,419,679 B1 * | 7/2002 | Dhindsa | 606/127 |
| 6,491,698 B1 * | 12/2002 | Bates et al. | 606/127 |
| 6,500,182 B2 * | 12/2002 | Foster | 606/127 |

(Continued)

FOREIGN PATENT DOCUMENTS

DE 197 22 429 A1 12/1998
EP 0 937 481 A1 8/1999

(Continued)

OTHER PUBLICATIONS

European Search Report and Annex (2 pages total) from corresponding European Patent Application No. EP 04 78 1437.

(Continued)

*Primary Examiner* — Elizabeth Houston
(74) *Attorney, Agent, or Firm* — Bookoff McAndrews, PLLC

(57) ABSTRACT

In an exemplary embodiment of the present disclosure, a medical device includes an elongate member and a retrieval assembly. The retrieval assembly extends distally from the elongate member and is formed from a same piece of material as the elongate member. The retrieval assembly is formed by removing at least a portion of the same piece of material.

25 Claims, 28 Drawing Sheets

U.S. PATENT DOCUMENTS

| | | | |
|---|---|---|---|
| 6,520,968 B2* | 2/2003 | Bates et al. | 606/113 |
| 6,527,781 B2* | 3/2003 | Bates et al. | 606/114 |
| 6,824,545 B2* | 11/2004 | Sepetka et al. | 606/113 |
| 6,942,673 B2* | 9/2005 | Bates et al. | 606/127 |
| 7,018,385 B2* | 3/2006 | Bates et al. | 606/127 |
| 7,022,102 B2* | 4/2006 | Paskar | 604/95.04 |
| 7,041,116 B2* | 5/2006 | Goto et al. | 606/200 |
| 7,077,849 B2* | 7/2006 | Bates et al. | 606/114 |
| 7,169,154 B1* | 1/2007 | Que et al. | 606/127 |
| 2002/0068944 A1* | 6/2002 | White et al. | 606/114 |
| 2002/0107526 A1* | 8/2002 | Greenberg et al. | 606/108 |
| 2003/0009208 A1 | 1/2003 | Snyder et al. | |
| 2003/0078593 A1* | 4/2003 | Bates et al. | 606/127 |
| 2003/0093087 A1* | 5/2003 | Jones et al. | 606/108 |
| 2003/0120281 A1* | 6/2003 | Bates et al. | 606/114 |
| 2003/0135233 A1* | 7/2003 | Bates et al. | 606/200 |
| 2004/0026942 A1* | 2/2004 | Kessler et al. | 294/100 |
| 2004/0054377 A1* | 3/2004 | Foster et al. | 606/167 |
| 2004/0087971 A1* | 5/2004 | Arnott | 606/127 |
| 2004/0138677 A1* | 7/2004 | Little et al. | 606/127 |
| 2004/0215212 A1* | 10/2004 | Teague et al. | 606/127 |
| 2005/0125004 A1* | 6/2005 | Bates et al. | 606/114 |
| 2005/0154378 A1* | 7/2005 | Teague et al. | 606/2.5 |
| 2005/0251151 A1* | 11/2005 | Teague | 606/113 |
| 2005/0261706 A1* | 11/2005 | Cheng et al. | 606/113 |
| 2006/0009786 A1* | 1/2006 | Bates et al. | 606/113 |
| 2006/0058813 A1* | 3/2006 | Teague et al. | 606/113 |
| 2006/0100641 A1* | 5/2006 | Teague | 606/113 |
| 2006/0161174 A1* | 7/2006 | Bates et al. | 606/114 |
| 2006/0190007 A1* | 8/2006 | Bates et al. | 606/113 |
| 2007/0073269 A1* | 3/2007 | Becker | 604/509 |
| 2007/0135820 A1* | 6/2007 | Que et al. | 606/127 |
| 2007/0288037 A1* | 12/2007 | Cheng et al. | 606/127 |

FOREIGN PATENT DOCUMENTS

| | | |
|---|---|---|
| WO | WO 00/76404 A2 | 12/2000 |
| WO | WO 01/97699 A1 | 12/2001 |

OTHER PUBLICATIONS

Official Communication from Counterpart Application EP 04 781 437.1 dated Jun. 27, 2008 (4 pages).

Communication Relating to the Results of the Partial International Search from International Application No. PCT/US2004/026742.

European Search Report and Annex (2 pages total) from corresponding European Patent Application No. EP 04 78 1437, Sep. 13, 2006.

Communication Relating to the Results of the Partial International Search from International Application No. PCT/US2004/026742, Dec. 30, 2004.

* cited by examiner

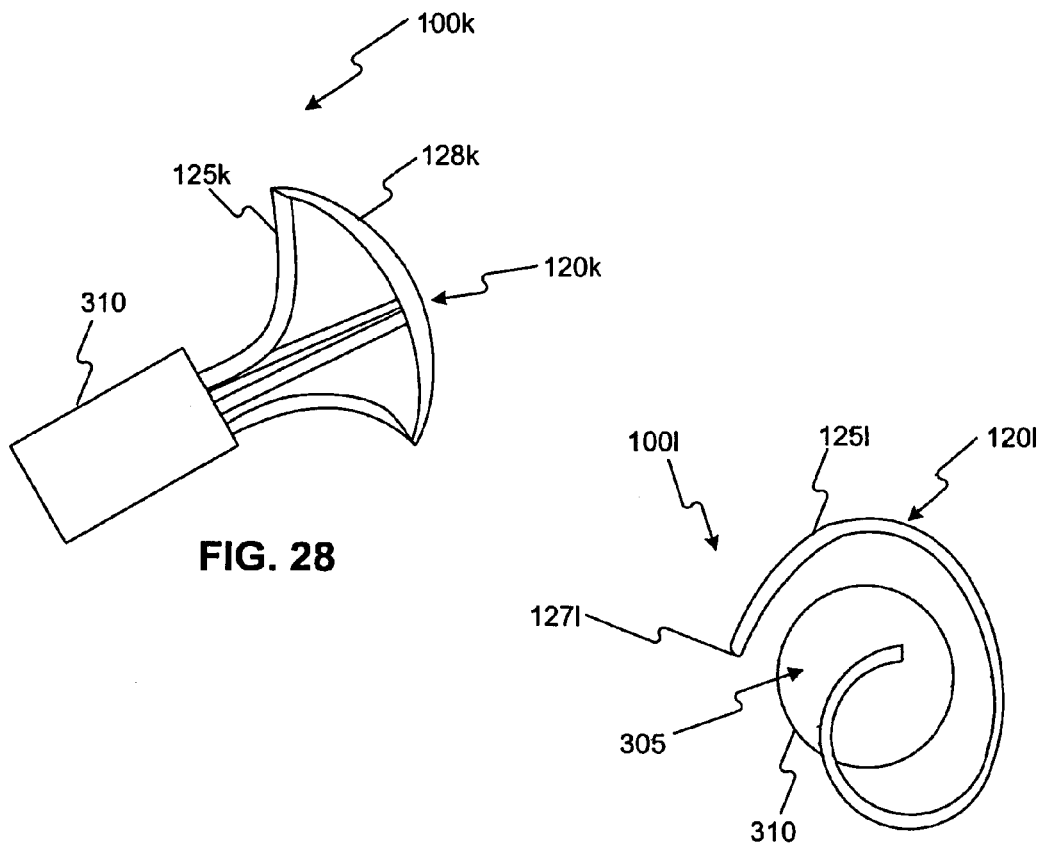
FIG. 28
FIG. 30
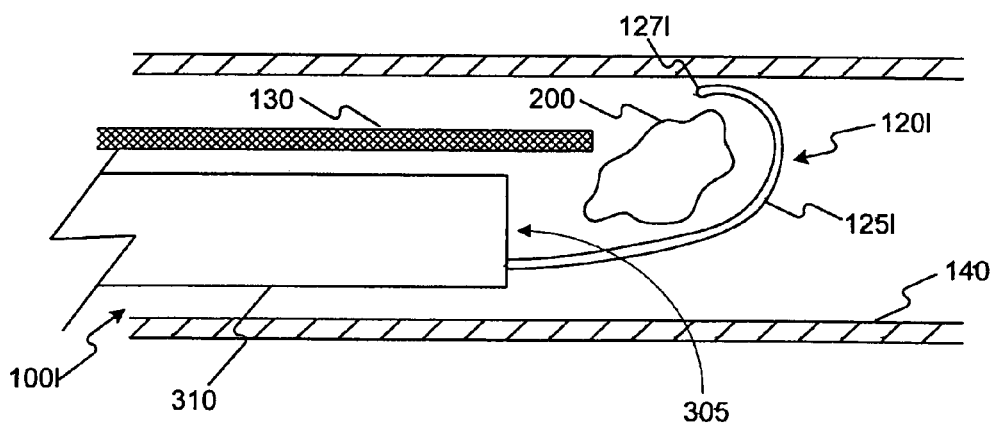
FIG. 29

MEDICAL RETRIEVAL DEVICES AND METHODS

CLAIM FOR PRIORITY

This application claims the benefit of U.S. Provisional Application No. 60/504,243, filed Sep. 18, 2003.

FIELD OF THE INVENTION

Embodiments of this invention generally relate to medical devices and procedures, and, more particularly, to medical devices and procedures for assisting in the removal of stones or other biological and/or foreign material from the body of a patient.

BACKGROUND OF THE INVENTION

A surgical retrieval device may be used, for example, to retrieve calculi from a body. The device may be used through an endoscope or a laparoscope, or it may be used without the aid of an endoscope or a laparoscope.

One type of surgical retrieval device has a sheath and a basket formed from wires. The basket is moveable in and out of the sheath. The basket may be collapsed within the sheath to achieve a reduced diameter profile. The basket may be opened when it extends beyond the distal end of the sheath.

Some retrieval devices include wires grouped together inside a cannula with the wires joined via soldering or welding to form a ball. Manufacturing of such devices may be costly and time consuming. Other devices have wires that are twisted and/or knotted together to eliminate a welded or soldered tip at the distal end of a basket. The tips of such devices may hinder access to calculi and may increase the possibility of tissue damage.

SUMMARY OF THE INVENTION

In accordance with one aspect of the present disclosure, a medical device includes an elongate member and a retrieval assembly extending distally from the elongate member and formed from a same piece of material as the elongate member. The retrieval assembly is formed by removing at least a portion of the same piece of material. In some embodiments, the same piece of material is a hollow tube. The retrieval assembly further includes at least one leg. In some embodiments, the device includes an optical fiber extending through a lumen defined by the tube, and the at least one leg may include a ramp portion to assist in positioning the optical fiber.

In another embodiment, the device includes a sheath defining a lumen, the retrieval assembly having a collapsed state in which the retrieval assembly is substantially disposed within the lumen of the sheath, and an expanded state in which the retrieval assembly is substantially outside of the lumen of the sheath. The sheath defines at least one cutout to alter the flexibility of the sheath. The retrieval assembly comprises a plurality of legs, each of the plurality of legs including a free distal end. In such an embodiment of the device, the plurality of legs are configured to transition from a substantially straight configuration when the retrieval assembly is in the collapsed state to a substantially curled configuration when the retrieval assembly is in the expanded state. Each of the plurality of legs, when in the substantially curled configuration, is curled back towards a proximal end of the device. The plurality of legs are configured to contact a biologic or foreign material in the substantially curled configuration to assist in removing the biologic or foreign material. The plurality of legs are configured to contact the biologic or foreign material as each free distal end is brought together by advancing the sheath toward the free distal ends. Each of the free distal ends includes at least one textured surface to assist in grasping the biologic or foreign material. In some embodiments, the elongate member defines at least one lumen. An optical fiber is disposed within the at least one lumen of the elongate member.

In other embodiments, at least one of the plurality of legs includes at least one textured surface to assist in grasping a material. In still other embodiments, the retrieval assembly further includes a plurality of legs and a tension member attached to each of the plurality of legs for manipulating a corresponding leg. Each tension member extends at least partially through a lumen defined by the elongate member. Each tension member is attached to a free end of the corresponding leg. Each tension member exits from an aperture defined by a side of the elongate member. In further embodiments, the elongate member defines at least one hole at a proximal end of the retrieval assembly, at least a portion of a proximal portion of the elongate member is removed to define corresponding interlocking portions, and the retrieval assembly further comprises a plurality of legs joined at a distal end. In an embodiment where the retrieval assembly further comprises a plurality of legs joined at a distal end, the device further includes a sheath defining a lumen, the retrieval assembly having a collapsed state in which the retrieval assembly is substantially disposed within the lumen of the sheath, and an expanded state in which the retrieval assembly is substantially outside of the lumen of the sheath.

In other embodiments, the retrieval assembly comprises two opposing loops configured to move toward each other when the retrieval assembly transitions from an expanded state to a collapsed state. Each of the two opposing loops includes a textured inward facing surface to assist in grasping biologic or foreign material. The two opposing loops are joined to form a single continuous loop having a curved state with a free proximal end when the retrieval assembly is in an expanded state. The retrieval assembly further includes netting attached to at least a portion of the continuous loop. In still other embodiments, the retrieval assembly includes a plurality of proximal legs extending to a plurality of distal legs, the distal legs being joined at a distal end of the retrieval assembly. The plurality of proximal legs includes a first proximal leg joining a proximal end of at least two of the plurality of distal legs, and a second proximal leg joining a proximal end of at least two other of the plurality of distal legs. The plurality of distal legs includes six legs. The retrieval assembly includes a continuous loop. The same piece of material is hollow and defines at least one lumen. The continuous loop includes a plurality of teeth. The distal end includes at least one spike. The retrieval assembly further includes a plurality of legs on only one side of the loop, each leg extending from a proximal end to a distal end of the loop.

In another embodiment of the present disclosure, a medical device includes a basket made of shape memory material and comprising a plurality of legs and a netting, a distal end of a first leg of the plurality of legs being configured to curve away from a distal end of a second leg of the plurality of legs when the basket is in a substantially open position, and the netting being connected to a distal end of each of the plurality of legs and an elongate member connected to a proximal end of the basket and disposed within a lumen of a sheath, the basket having a collapsed state in which the basket is substantially disposed within the lumen of the sheath, and an expanded state in which the basket is substantially outside of the lumen of the sheath. In such an embodiment, the netting is made of shape memory material. The basket is configured to assume an umbrella-like shape in the expanded state to assist in immobilizing a stone. Each of the plurality of legs are substantially evenly spaced apart.

In still another embodiment of the present disclosure, a medical device includes a basket made of shape memory material and comprising a substantially spiral-shaped leg and a free distal end curved toward a proximal end of the leg and an elongate member connected to a proximal end of the basket and disposed within a lumen of a sheath of the device, the basket having a collapsed state in which the basket is substantially disposed within the lumen of the sheath and an expanded state in which the basket is substantially outside of the lumen of the sheath. The basket includes a single leg.

In a further embodiment of the present disclosure, a medical device includes a sheath defining a lumen, an elongate actuation member disposed within the lumen of the sheath and longitudinally moveable relative to the sheath, and a basket including a plurality of legs, a distal end of each of the plurality of legs being fixed to the sheath, a proximal end of each of the plurality of legs being fixed to the elongate actuation member, wherein movement of the elongate actuation member distally relative to the sheath expands the basket. The distal end of each of the plurality of legs is fixed a distal end of the sheath. The device includes a crimp ring configured to fixedly connect each of the plurality of legs to the sheath. The crimp ring fixedly connects each of the plurality of legs to an inner surface of the sheath. At least a portion of each of the plurality of legs extends proximate to an outside surface of the sheath when the basket is in a closed position. The sheath defines a plurality of ports along a length of the sheath, the ports configured to accept at least one of the plurality of legs. The number of the plurality of ports is equal to the number of the plurality of legs. Each of the plurality of legs is made of a shape memory material. The elongate actuation member is hollow and a proximal end of each of the plurality of legs is connected to a distal end of the elongate actuation member.

In another embodiment of the present disclosure, a medical device includes a sheath defining a lumen, an elongate actuation member disposed within the lumen of the sheath and longitudinally moveable relative to the sheath, a stabilizing member at least partially disposed within a lumen of the elongate actuation member, the stabilizing member being longitudinally moveable relative to the elongate actuation member, and a basket including a plurality of legs, a distal end of each of the plurality of legs being coupled to the stabilizing member, a proximal end of each of the plurality of legs being coupled to the elongate actuation member, and at least a portion of each of the plurality of legs extending proximate to an outside surface of the sheath when the basket is in a closed position. The sheath defines a plurality of ports along a length of the sheath, the ports configured to accept at least one of the plurality of legs. The number of the plurality of ports is equal to the number of the plurality of legs. The basket is configured to transition between an expanded position and a collapsed position by manipulating the elongate actuation member relative to the stabilizing member.

In still another embodiment of the present disclosure, a medical device includes a sheath defining a lumen, an elongate actuation member disposed within the lumen of the sheath and longitudinally moveable relative to the sheath, a stabilizing member at least partially disposed within the elongate actuation member and longitudinally moveable relative to the elongate actuation member within the lumen of the sheath, and a basket including a plurality of legs, a distal end of each of the plurality of legs being fixed to a distal end of the stabilizing member, a proximal end of each of the plurality of legs being fixed to the elongate actuation member, and each of the plurality of legs being substantially entirely disposed within the lumen of the sheath when the basket is in a closed position. At least a portion of the basket expands from a distal end of the sheath as the elongate actuation member is advanced toward the distal end of the sheath.

In yet another embodiment of the present disclosure, a medical device includes a sheath defining a lumen, an elongate actuation member disposed within the lumen of the sheath and longitudinally moveable relative to the sheath, a proximal basket including a plurality of proximal legs, a distal end of each of the plurality of proximal legs being connected to a surface of the sheath, and a distal basket including a plurality of distal legs, a proximal end of each of the plurality of distal legs being connected to a distal end of the elongate actuation member. At least a portion of the basket expands from a distal end of the sheath as the elongate actuation member is advanced toward the distal end of the sheath.

In still another embodiment of the present disclosure, a medical device includes a sheath defining a lumen, an elongate actuation member disposed within the lumen of the sheath and longitudinally moveable relative to the sheath, a proximal basket including a plurality of proximal legs, a distal end of each of the plurality of proximal legs being connected to a surface of the sheath, and a distal basket including a plurality of distal legs, a proximal end of each of the plurality of distal legs being connected to a distal end of the elongate actuation member. The surface of the sheath is an inner surface of the sheath. A proximal end of each of the plurality of proximal legs is connected to the elongate actuation member and the elongate actuation member is configured to manipulate at least a portion of the proximal basket. The sheath defines a plurality of ports configured to accept at least one of the plurality of proximal legs. In such a device, the number of the plurality of ports is equal to the number of the plurality of proximal legs. At least a portion of each of the plurality of proximal legs extends proximate to an outside surface of the sheath when the proximal basket is in a closed position. The proximal basket and the distal basket are configured to transition between respective expanded positions and collapsed positions substantially in unison. Such a device, also includes an extending member disposed within the at least one lumen of the sheath and defining an extending member lumen, the elongate actuation member being disposed within the extending member lumen. A proximal end of each of the plurality of proximal legs is connected to the extending member. The sheath defines a plurality of ports configured to accept at least one of the plurality of proximal legs. The number of the plurality of ports is equal to the number of the plurality of proximal legs. At least a portion of each of the plurality of proximal legs extends proximate to an outside surface of the sheath when the proximal basket is in a closed position. The proximal basket and the distal basket are independently maneuverable.

In a further embodiment of the present disclosure, a medical device includes a sheath defining a lumen, a shaft disposed within the lumen and moveable relative to the lumen, and a retrieval assembly including a plurality of legs comprising a shape memory material, each of the plurality of legs having a proximal end fixedly attached to a distal end of the shaft, and a free distal end extending in a proximal direction beyond the distal end of the shaft when the retrieval assembly is in a substantially expanded position. Each of the plurality of legs is formed of the shaft. The retrieval assembly achieves the substantially expanded position as the sheath is moved in a proximal direction relative to the shaft. Each of the plurality of legs achieves a substantially circular shape when the retrieval assembly is in the substantially expanded position.

In yet another embodiment of the present disclosure, a method of making a medical device includes providing an elongate member, and removing at least a portion of the elongate member to form a retrieval assembly, the retrieval assembly comprising at least two loops, each of the at least two loops having a proximal end integral with the elongate member. The method may further include forming a plurality of teeth on a surface of each of the at least two loops, removing at least a portion of a proximal portion of the elongate member to define corresponding interlocking portions, forming at least one hole at the proximal ends of the at least two loops, and detaching a portion of each of the at least two loops from the elongate member so as to form a single loop, the single loop having a free distal end and a proximal end that is connected to the elongate member. The at least two loops are connected only at the proximal ends. The method may further include providing a netting connected to at least a portion of the single loop.

In another embodiment of the present disclosure, a method of making a medical device includes providing an elongate member and removing a portion of the elongate member to form a retrieval assembly, the retrieval assembly comprising at least two proximal legs extending to a plurality of distal legs, each of the plurality of distal legs being connected at a distal end portion of the retrieval assembly. The removing step includes first removing a portion of the elongate member to form two legs and then removing a portion of the two legs to form the two proximal legs and the plurality of distal legs. The elongate member defines at least one lumen.

In another embodiment of the present disclosure, a method for removing a stone from a body includes providing a medical device comprising an elongate member and a retrieval assembly comprising a plurality of legs, a proximal end of each of the plurality of legs being connected to the elongate member and a distal end of each of the plurality of legs being connected to a corresponding tension member, positioning the retrieval assembly adjacent to the stone, expanding the retrieval assembly by releasing the tension members, and capturing the stone with the retrieval assembly. The capturing the stone further includes manipulating at least one of the tension members toward a proximal end of the device. The method may further include manipulating each of the legs independently via the corresponding tension members. Each of the tension members extends through a lumen of the elongate member.

In further embodiments, a method for immobilizing a stone within a body includes providing a medical device comprising a sheath, an elongate actuation member disposed within a lumen of the sheath, a proximal basket including a plurality of proximal legs, and a distal basket including a plurality of distal legs, positioning a distal end of the sheath distal the stone, expanding the distal basket, and expanding the proximal basket. The expanding the distal basket includes manipulating the elongate actuation member in a distal direction. The expanding the proximal basket includes manipulating the elongate actuation member in a distal direction. The proximal basket and the distal basket expand in unison. The expanding the proximal basket includes manipulating an extending member disposed within the lumen of the sheath and moveable independent of the elongate actuation member. The proximal basket and the distal basket expand independently. The proximal basket is expanded proximal to the stone and the distal basket is expanded distal to the stone.

Both the foregoing general description and the following detailed description are exemplary and explanatory only, and are not restrictive of the invention as claimed.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 28 is a plan view of the device of FIG. 26.

FIG. 29 is an operational view of a portion of a stone removal assistance device according to still another embodiment of the present disclosure.

FIG. 30 is an end view of the device of FIG. 29.

DETAILED DESCRIPTION

The present disclosure generally relates to devices and methods for the retrieval of material from the body of a patient. The devices and methods may permit eased capture of material and may prevent damage to the lining of the body tract in which the material resides. Features of the present disclosure may also be advantageous in clinical situations where the material must be released and the device must be withdrawn from the body.

Figure 1:
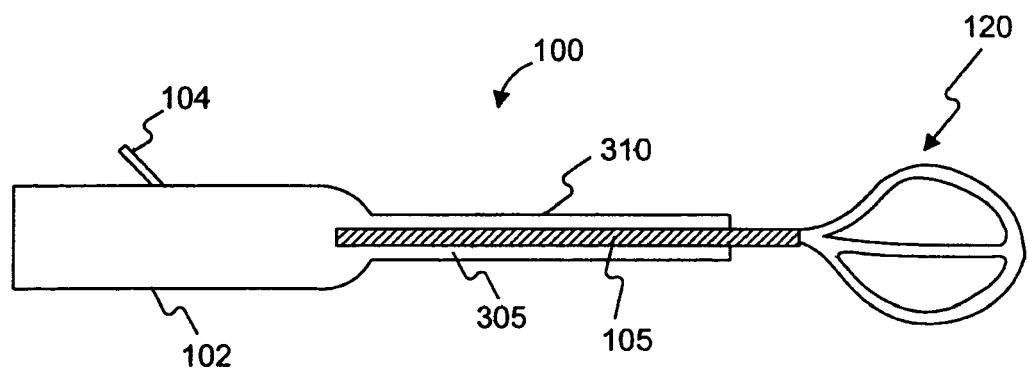
FIG. 1 is a cross-sectional view of a stone removal assistance device according to an exemplary embodiment of the present disclosure.

FIG. 1 is an exemplary cross-sectional view of a stone removal assistance device 100 including a retrieval assembly 120 in an extended and expanded position according to an illustrative embodiment of the invention. The device 100 may include a handle 102, a sheath 310, and a retrieval assembly 120 moveable in a lumen 305 of the sheath 310. The handle 102, the sheath 310, and the retrieval assembly 120 illustrated in FIG. 1 are not shown in their correct size or proportion to each other, and the sheath 310 may typically be much longer than the handle 102 or the retrieval assembly 120 to allow insertion into a body cavity, canal, or tract. The sheath 310 may be dimensioned based on the requirements of the application of the sheath 310 within the body. For example, for urological applications, the sheath 310 may be of a length capable of extending into, for example, any upper calyx of the bladder of a patient. The sheath 310 may be made of commonly available materials that provide sufficient strength and flexibility for adequate operation, but which are soft enough to avoid trauma or irritation to the tract or duct in which sheath 310 is deployed. Materials that may commonly be used to form sheath 310 include polyethylene, nylons, polyether block amide, polytetrafluoroethylene, urethanes, silicones, and other suitable polymer materials. The material used is preferably biocompatible and inert to body fluids.

As shown in FIG. 1, other features of the device 100 may include, for example, an elongate member 105, such as a cable, coil, shaft, cannula, tube, or mandril wire, that extends within the lumen 305 of the sheath 310, and at least one actuating mechanism 104. Operation of the actuating mechanism 104 may cause, for example, the retrieval assembly 120 to move into and out of the lumen 305 of the sheath 310. Alternatively, the actuating mechanism 104 may cause movement of the sheath 310 to advance the sheath 310 over a stationary retrieval assembly 120 and elongate member 105 to thereby enclose the retrieval assembly 120 within the sheath 310. In such an embodiment, the actuating mechanism 104 may be manipulated to slide the moveable sheath 310 back to expose the stationary retrieval assembly 120.

Figure 2:
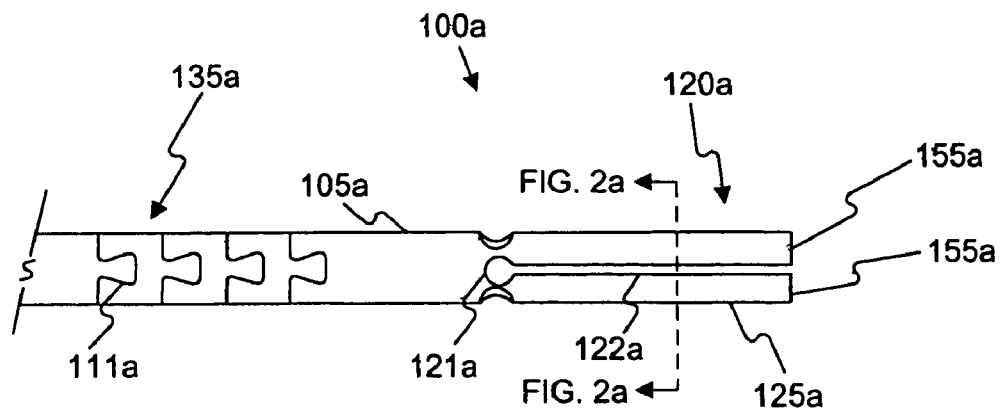
FIG. 2 is a side view of a portion of a stone removal assistance device according to an exemplary embodiment of the present disclosure.
Figure 2A:
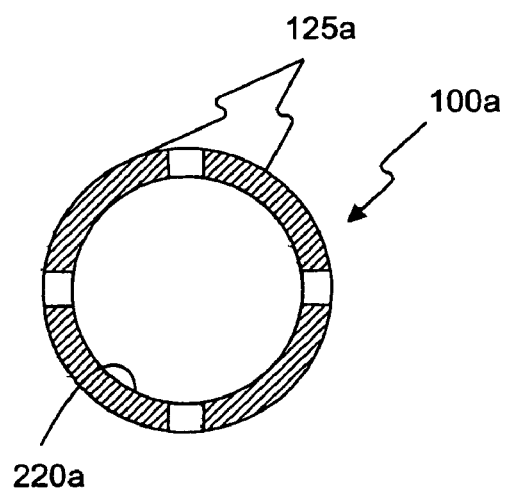
FIG. 2a is a cross-sectional view of the device illustrated in FIG. 2.

Referring to FIGS. 2 and 2a, an embodiment of a stone removal assistance device 100a may include an elongate member 105a that may be formed, for example, from a rod, cannula, or hollow tube. The elongate member 105a may include a proximal portion 135a and a retrieval assembly 120a. Thus, the proximal portion 135a and the retrieval assembly 120a may be formed from the same piece of material. The retrieval assembly 120a may include one or more legs 125a, and each of the legs 125a may have a free distal end 155a. In addition, one or more of the legs 125a may have an inner surface 220a, as shown in FIG. 2, that may be smooth or textured. Such a textured inner surface 220a may assist in securing material when grasped in the retrieval assembly 120a. As will be described in greater detail below, any variety of texture useful in assisting in grasping material may be used.

The legs 125a may be formed by, for example, laser cutting, chemical etching, or mechanically slicing the elongate member 105a. The elongate member 105a may be made of, for example, stainless steel (such as 300 and 400 series), cobalt chromium, nickel titanium, a thermoforming plastic, or other material that is biocompatible for surgical purposes. Other optional materials include, for example, polytetrafluoroethylene ("PTFE"), expanded polytetrafluoroethylene ("EPTFE"), or GoreTex™. The elongate member 105a may be highly polished to improve laser light reflectivity and may include a polymer coated with a metal or a metal coated with a polymer. Thus, the elongate member 105a may have more than one layer. These same materials, or combinations thereof, may also be used to form the sheaths, elongate members, and/or other structures of the devices of the present disclosure.

With continued reference to FIG. 2, slots 122a may be cut into the elongate member 105a to define the legs 125a of the retrieval assembly 120a. The width of the slots 122a may be selected to control the width and/or mechanical behavior of the legs 125a. Stress relief features 121a may be defined at proximal end of the legs 125a. A stress relief feature 121a may be any shape that effectively reduces mechanical stress at the end of the associated slot and/or facilitates movement of the legs 125a neighboring the stress relief feature 121a. For example, in one embodiment, a stress relief feature 121a may be a hole at the proximal end of the slot 122a having a diameter that is greater than the width of the slot 122a.

Flexibility features 111a may be cut into the proximal portion 135a to increase the flexibility of the proximal portion 135a when maneuvering the device 100a within the body of a patient. The flexibility features 111a may be positioned anywhere along a portion of the proximal portion 135a in order to impart a desired flexibility to portions of the device 100a. The cut for each flexibility feature 111a may extend partially or completely through the wall of the elongate member 105a and may extend partially or completely around the circumference of the elongate member 105a. When extending completely around the circumference, the flexibility feature 111a may define a shape, such as the illustrated zigzag shape, to effectively interlock neighboring portions of the elongate member 105a that are separated by the cut. The flexibility features 111a may improve the ability of the device 100a to pass through complex body structures.

Figure 3:
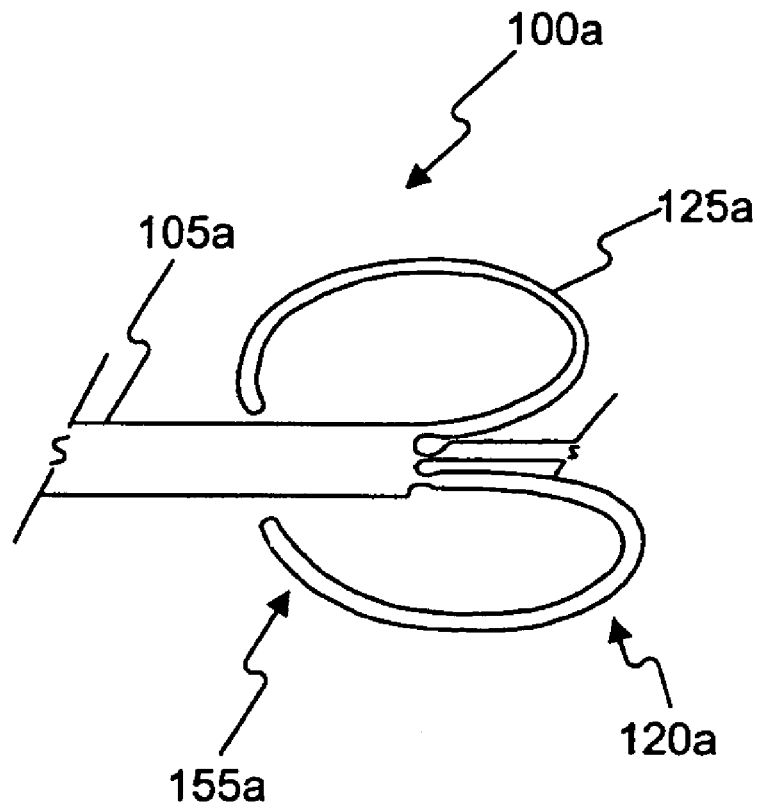
FIG. 3 is a partial view of the device of FIG. 2.

The retrieval assembly 120a may have a closed state (FIG. 2) and an open state (FIG. 3). Referring to FIG. 3, the legs 125a of the retrieval assembly 120a may be arranged in any configuration useful for grasping stones or other material when in the open state. The shape of a leg 125a may be produced, for example, by cold working and/or hot working. Each of the legs 125a may have a similar shape, or alternatively, each of the legs 125a may have different shapes. For example, the legs 125a may all be substantially straight and free at their distal ends 155a to permit grasping of an object in a tweezer-like manner. As shown in FIG. 3, the retrieval assembly 120a may include legs 125a that curl back in the proximal direction when the retrieval assembly 120a is in an open state. When in the open state, the retrieval assembly 120a may have a diameter, for example, of approximately 1.5 cm to approximately 2.5 cm. The shape and size of the retrieval assembly 120a may be selected to assist in capturing, for example, a calculi within the urinary tract of a patient.

Figure 4:
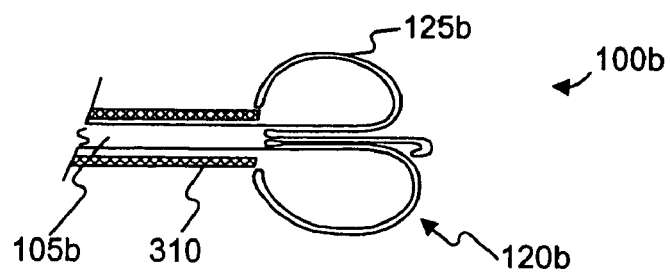
FIG. 4 is a cross-sectional view of a portion of a stone removal assistance device according to another embodiment of the present disclosure.
Figure 5:
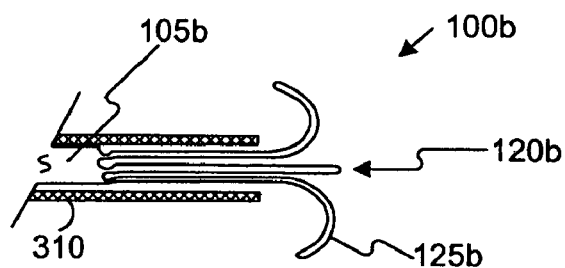
FIG. 5 is a cross-sectional view of the device of FIG. 4.
Figure 6:
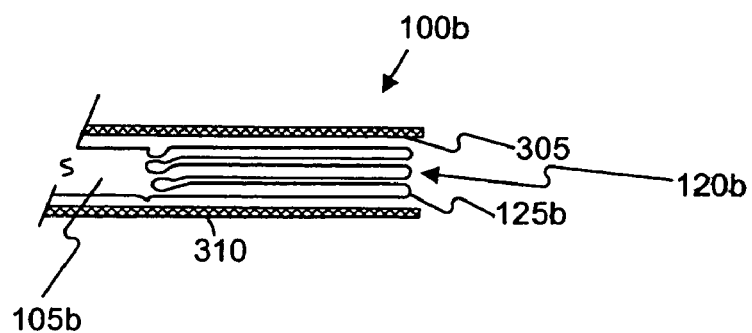
FIG. 6 is another cross-sectional view of the device of FIG. 4.

FIGS. 4, 5, and 6 illustrate the functioning of a stone removal assistance device 100b according to another embodiment of the present disclosure. FIG. 4 shows an embodiment of the device 100b in an open state. In this embodiment, the device 100b may include an elongate member 105b and a sheath 310. This sheath 310 may be moveable relative to the elongate member 105b to facilitate opening and closing of the retrieval assembly 120b.

As shown in FIG. 5, the legs 125b may at least partially enter the sheath 310 and the retrieval assembly 120b may transition to the closed state as the sheath 310 is moved in the distal direction relative to the retrieval assembly 120b. FIG. 6 illustrates the retrieval assembly 120b in the fully closed, or collapsed, state with the legs 125b fully within a lumen 305 of the sheath 310.

Figure 7:
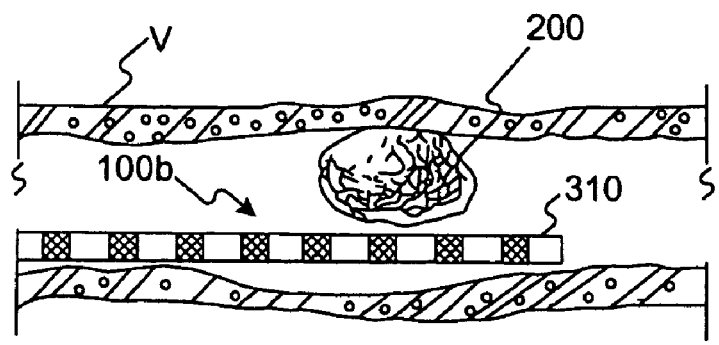
FIG. 7 is an operational view of the device of FIG. 4.
Figure 8:
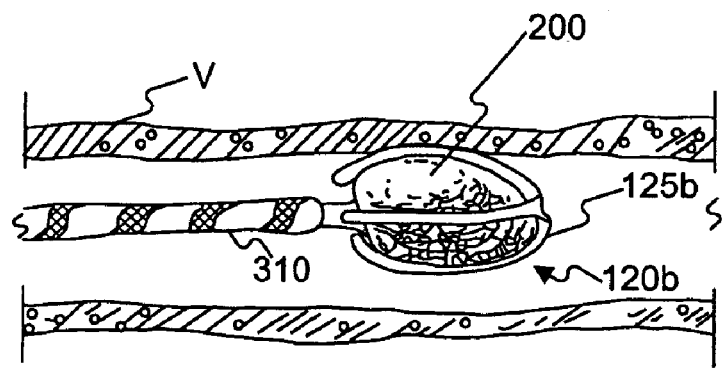
FIG. 8 is another operational view of the device of FIG. 4.

As shown in FIG. 7, the device 100b may be inserted into a vessel V of a patient while the retrieval assembly 120b (not shown) is in a closed position. The vessel V may be, for example, a portion of the patient's urinary tract. The sheath 310 may be placed adjacent to a stone 200 in the vessel V to appropriately position the legs 125b of the retrieval assembly 120b next to the stone 200 while within the sheath 310. Preferably, the distal end of sheath 310 is placed past, or distal to, the stone 200. The sheath 310 may then be retracted to permit the legs 125b to transition to the open state and capture the stone (FIG. 8). The legs 125b may be moved in the proximal direction to assist in capturing the stone 200.

The stone 200 may be a kidney stone, a struvite, a uric acid stone, a gallbladder stone, a cystine stone, or other solid deposit commonly removed from a body structure or vessel of a patient. Such stones 200 may contain various combinations of chemicals including, but not limited to, calcium, oxalate, and phosphate. The stone 200 may be of any size or shape, and could be, for example, flat, round, smooth, or jagged. Although FIGS. 7 and 8 show a stone 200 in close proximity to the vessel V, devices of the present disclosure may assist in the immobilization and removal of stones that are both impacted and free floating. Furthermore, while the devices of the present disclosure may assist in manipulating, capturing, fragmenting, reducing the size of, and/or removing stones 200 of the type described above, the devices may also assist in manipulating, capturing, fragmenting, reducing the size of, and/or removing any other type of biological, foreign, and/or other matter from within the body of a patient.

Figure 22:
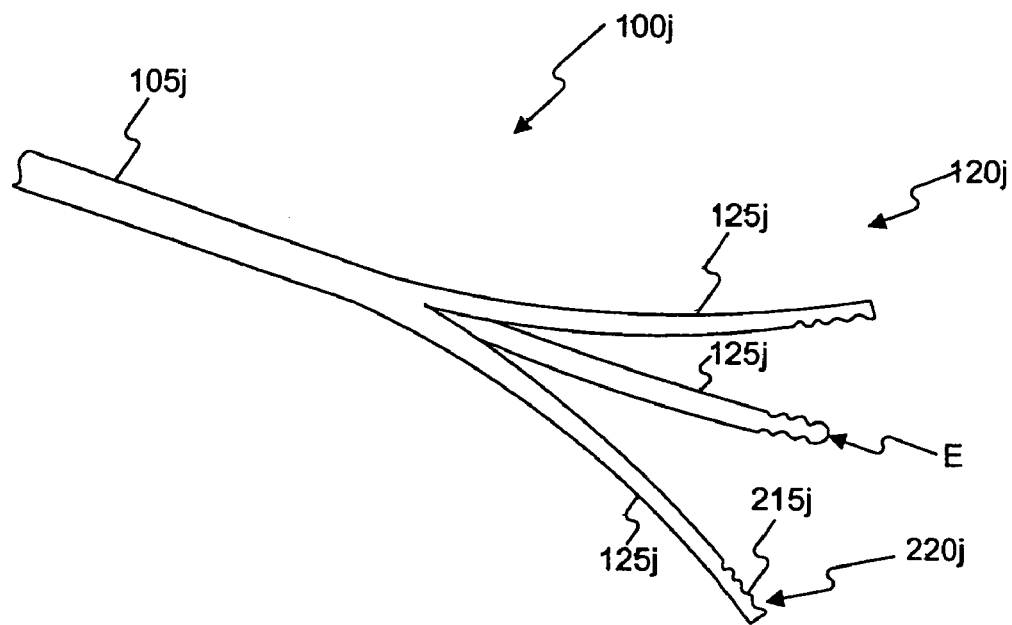
FIG. 22 is a plan view of a portion of a stone removal assistance device according to yet another embodiment of the present disclosure.
Figure 23:
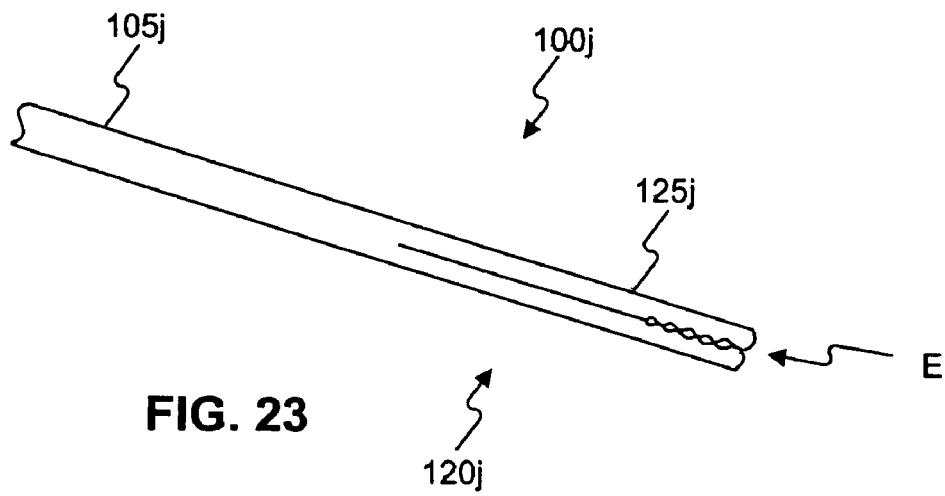
FIG. 23 is a side view of the device of FIG. 22.
Figure 24:
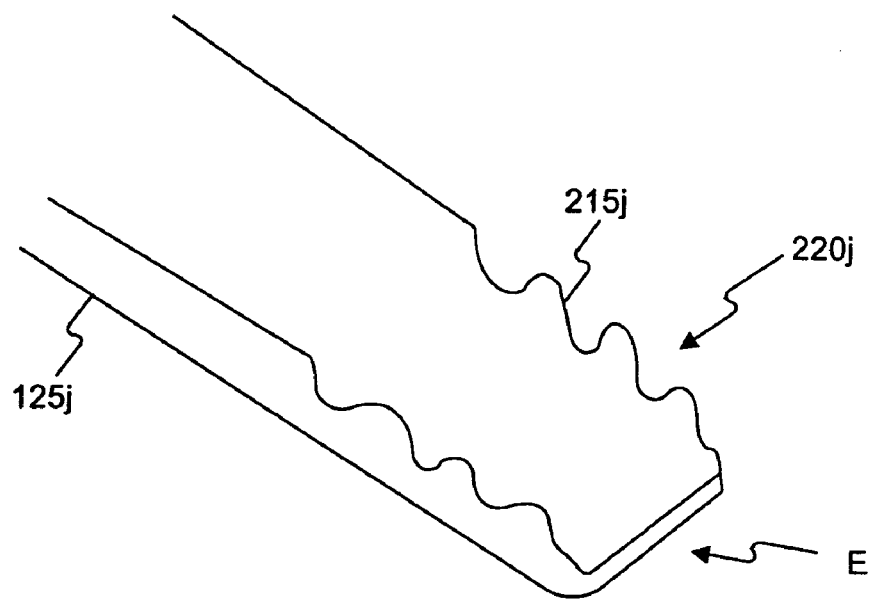
FIG. 24 is a portion of a leg of the device of FIG. 22.

As another example of a stone removal assistance device formed from a single piece of material, FIGS. 22-24 show an embodiment of a portion of a device 100j that includes an elongate member 105j and a grasping assembly 120j formed from a distal portion of the elongate member 105j. The grasping assembly 120j includes legs 125j that have a free end E and that are substantially straight when the grasping assembly 120j is in the open state. Particularly, legs 125j are curved slightly outward when in the open, unrestrained state.

The legs 125j may be gradually collapsed to grasp and hold a stone 200 (FIG. 25) by moving a sheath (not shown) at least partially over the grasping assembly 120j. The legs 125j may thus be operated in a tweezer-like manner.

The legs 125j may be provided with at least one textured surface 220j to assist grasping of a material. Texture imparted to the surface 220j may be formed, for example, by cutting, etching, sand blasting, or by a variety of other known techniques. These techniques may create any desirable contact feature 215j such as, for example, serrations or pitting useful in gripping and controlling material such as a stone. As shown in FIG. 24, in some embodiments, the textured surface 220j may include teeth 215j.

Figure 25:
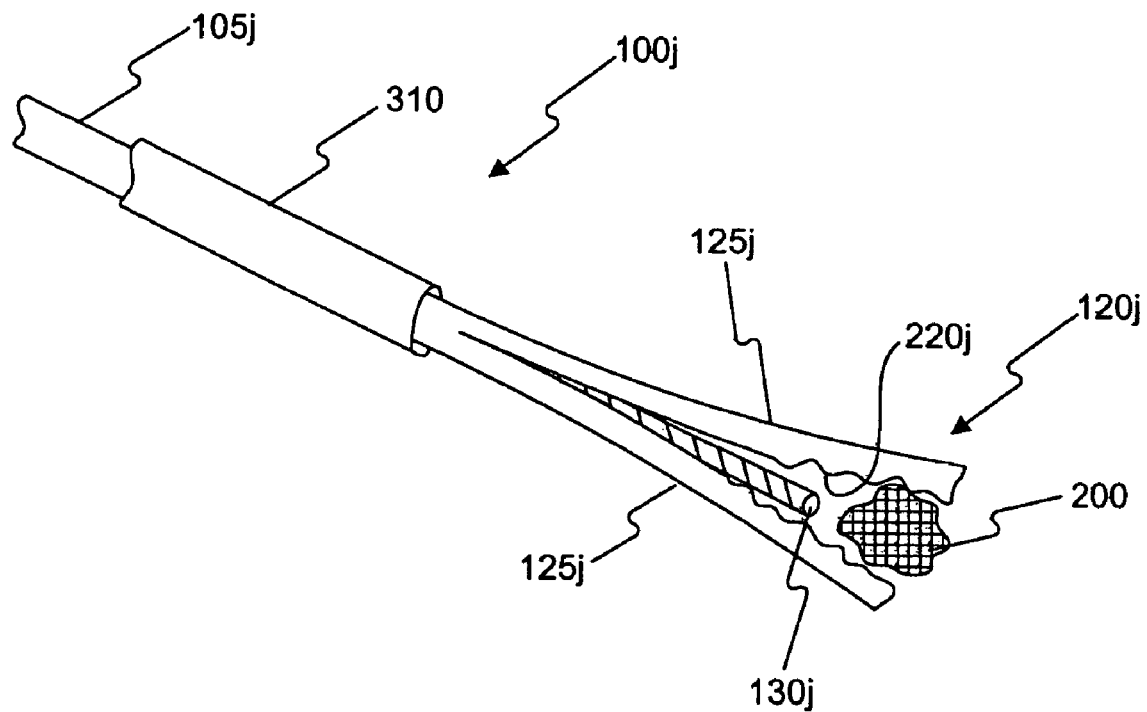
FIG. 25 is an operational view of the device of FIG. 22.

FIG. 25 illustrates a use of the device 100j of FIGS. 22-24 for laser lithotripsy. After capture of a stone 200 by the legs 125j, an optical fiber 130j may be moved through a lumen of the elongate member 105j until the end of the fiber 130j is appropriately positioned next to the stone 200. Laser light may then be directed toward the stone 200 to break up and/or dissolve the stone 200.

Referring back to FIG. 9, another embodiment of a stone removal assistance device 100c according to principles of the present disclosure includes a laser light component 130, such as an optical fiber, a cannula 110c defining a lumen 306c, and a retrieval assembly 120c including a leg 125c having a ramp portion 115c. The laser light component 130 may be directed along the lumen 306c of the cannula 110c and positioned adjacent to a stone 200 trapped by the device 100c. The ramp portion 115c may be shaped to direct the laser light component 130 toward the stone 200 when the laser light component 130 exits the lumen 306c of the cannula 110c. For example, ramp portion 115c may comprise a portion of leg 125c raised or otherwise directed to an inward surface of leg 125c when leg 125c is in an open and/or curled state. In that way, ramp portion 115c may contact a distal end of laser light component 130 to deflect component 130 toward the stone 200. Laser light may then be directed upon the stone 200, for example, for laser lithotripsy. Moreover, in the curled state, leg 125c may define a substantially enclosed area and a bend having a point directed towards the substantially enclosed area. The bend may be greater than 90 degrees.

Figure 10:
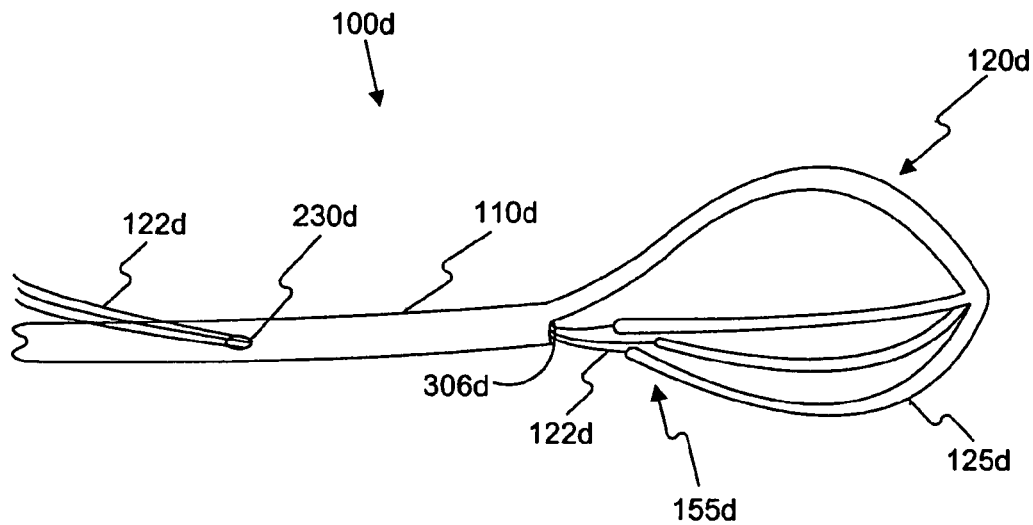
FIG. 10 is a side view of a portion of a stone removal assistance device according to still another embodiment of the present disclosure.

FIG. 10 shows another embodiment of a stone removal assistance device 100d. The device 100d includes a cannula 110d that defines a lumen 306d. The device 100d has a retrieval assembly 120d that includes two or more legs 125d. Part of the cannula 110d may be connected to one or more of the legs 125d to define the retrieval assembly 120d for trapping stones or other material in a patient's body. The cannula 110d and the legs 125d may cooperate to grasp a stone (not shown).

The device 100d may include one or more tension members 122d, such as a thread, joined to the distal ends 155d of one or more of the legs 125d. FIG. 10 shows three such tension members 122d, one corresponding to each leg 125d. Alternatively, a single tension member 122d may attach to more than one leg 125d or all of the legs 125d. Pulling on the tension members 122d may provide control for grasping and/or releasing a stone. The tension members 122d may extend within the lumen 306d of the cannula 110d and may exit from an aperture 230d in the wall of the cannula 110d. Alternatively, tension members 122d may extend completely through cannula 110d and exit cannula 110d at a proximal most end. In operation, the tension members 122d may be released to permit the retrieval assembly 120d to extend and collapse as a sheath (not shown) is moved over the retrieval assembly 120d.

Figure 11:
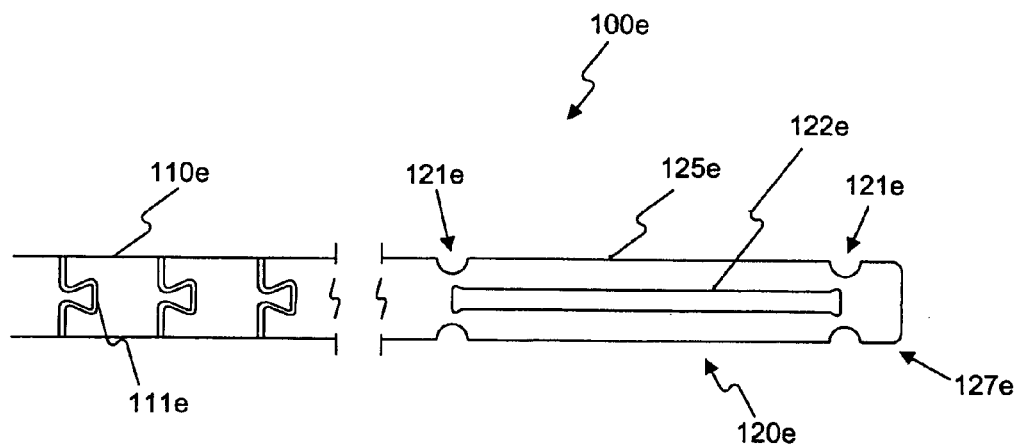
FIG. 11 is a side view of a portion of a stone removal assistance device according to yet another embodiment of the present disclosure.
Figure 12:
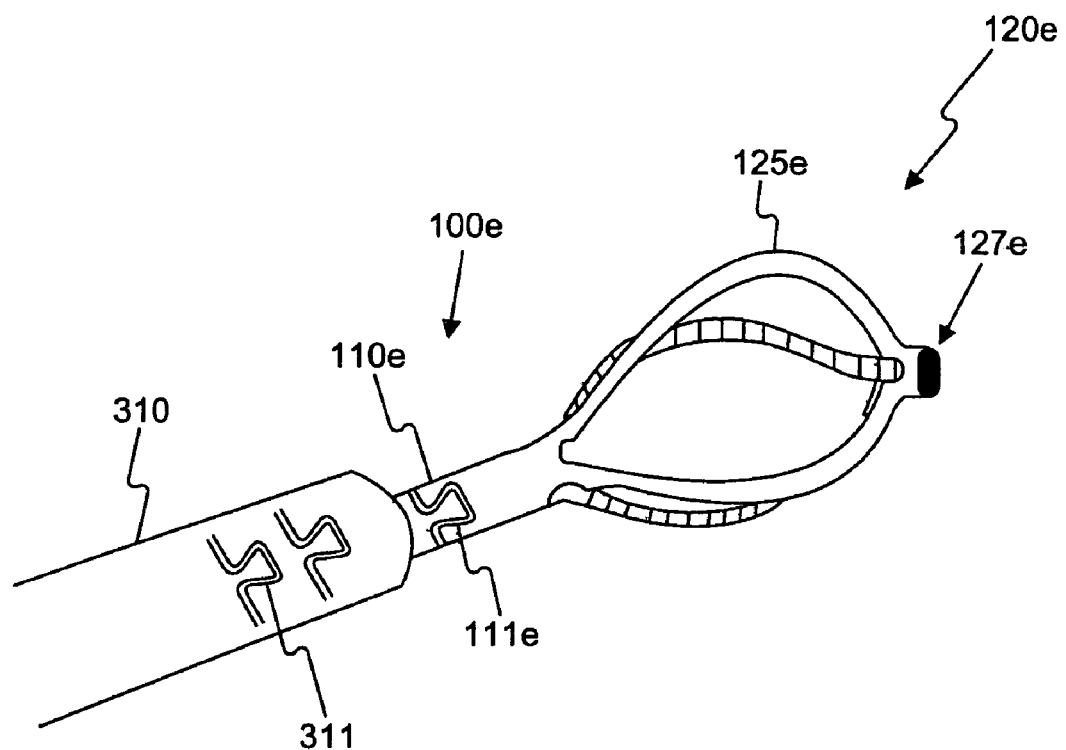
FIG. 12 is a plan view of the device of FIG. 11.

FIGS. 11 and 12 show another embodiment of a stone removal assistance device 100e. The device 100e may include a substantially hollow proximal portion or cannula 110e, a retrieval assembly 120e including two or more legs 125e, and a distal end 127e that joins the two or more legs 125e together. The cannula 110e and the retrieval assembly 120e may be formed from a single piece of tubing. The device 100e may be mechanically similar to the device 100a of FIGS. 2 and 3 except that the slots 122e may not extend completely in the distal direction, thus forming distal end 127e.

In some embodiments, the device 100e may include a sheath 310 (FIG. 12). In such embodiments, the sheath 310 may include cutouts 311 to increase the flexibility of the sheath 310. The cutouts 311 may be substantially the same as the flexibility features 111 described above. As shown in FIG. 12, the cannula 110e may include at least one flexibility feature 111e. In addition, the distal end 127e may be filled with, for example, epoxy or brazing material. Since the distal end may be formed from the hollow cannula 110e in some embodiments, the epoxy or brazing material may at least partially fill a hole defined by an inner diameter of the hollow cannula 110e.

Figure 13:
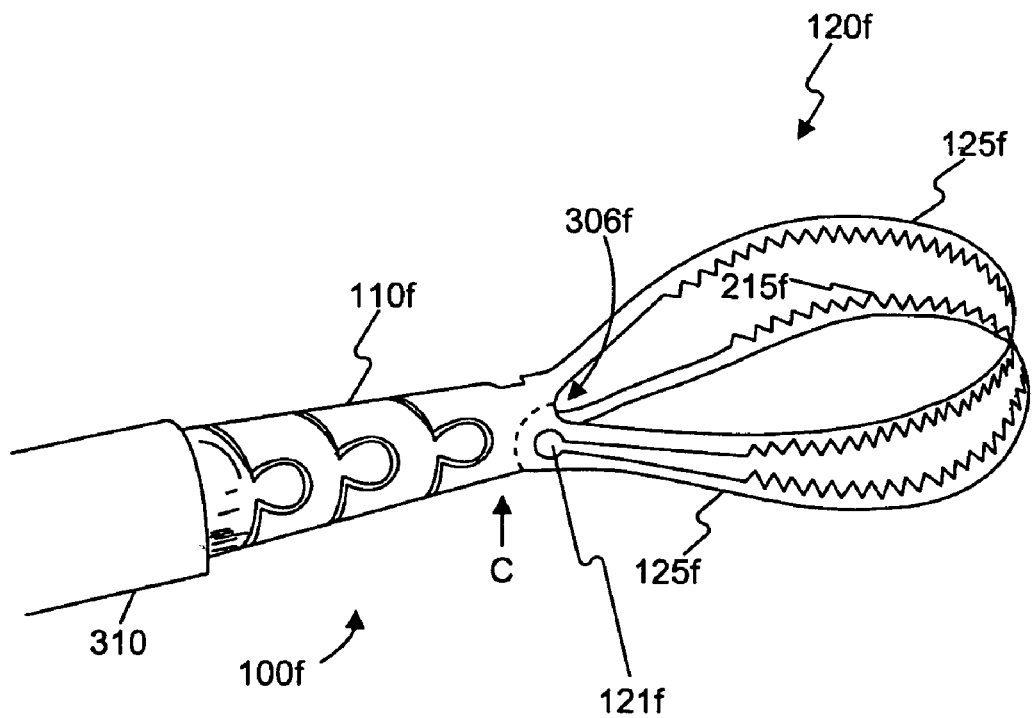
FIG. 13 is a plan view of a portion of a stone removal assistance device according to a further embodiment of the present disclosure.

FIGS. 13-17 show another embodiment of a stone removal assistance device 100f. The device 100f includes a sheath 310, a cannula 110f that defines a lumen 306f, and a retrieval assembly 120f including four legs 125f joined in two pairs, each pair defining a loop. As described above with respect to FIGS. 22-25, each leg 125f may include one or more contact features 215f, for example, on inward-facing surfaces, to assist in, for example, gripping a stone. The device 100f may further include at least one stress relief feature 121f defined at the proximal end of the legs 125f. As explained with respect to FIG. 2, the stress relief features 121f may be any shape that effectively reduces mechanical stress at the end of the associated legs 125f and may facilitate movement of the legs 125f neighboring the stress relief feature 121f. As shown in FIG. 13, the stress relief feature 121f may be a hole at the proximal end of legs 125f.

Figure 14:
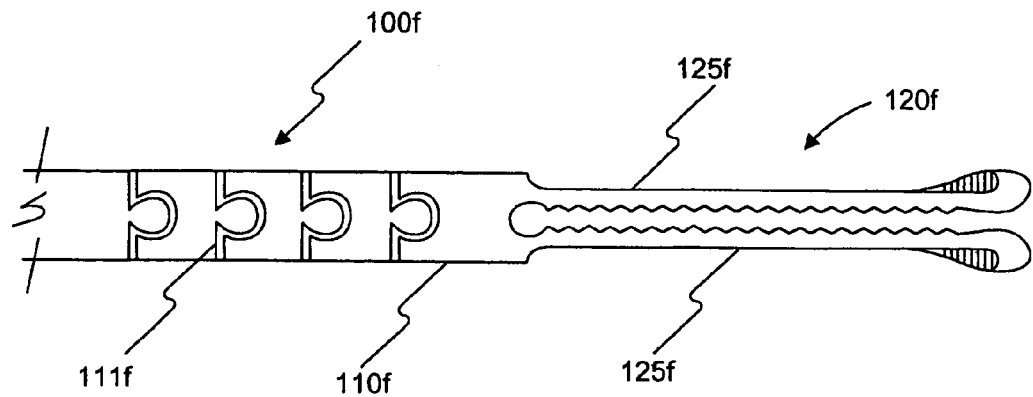
FIG. 14 is a side view of the device of FIG. 13.
Figure 15:
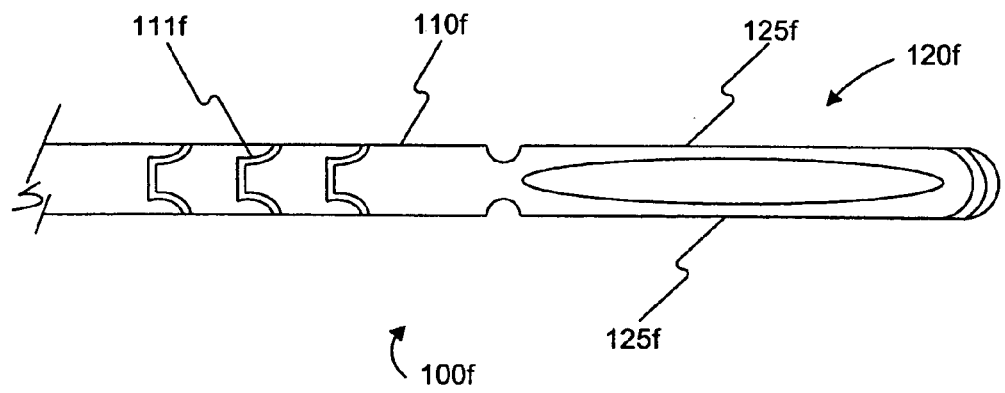
FIG. 15 is a top view of the device of FIG. 14.
Figure 16:
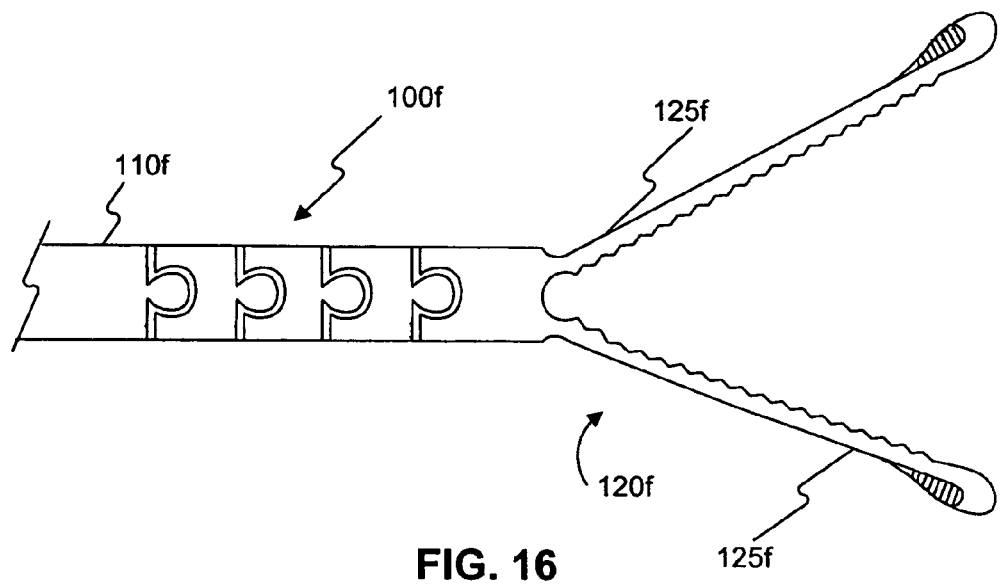
FIG. 16 is another side view of the device of FIG. 13.
Figure 17:
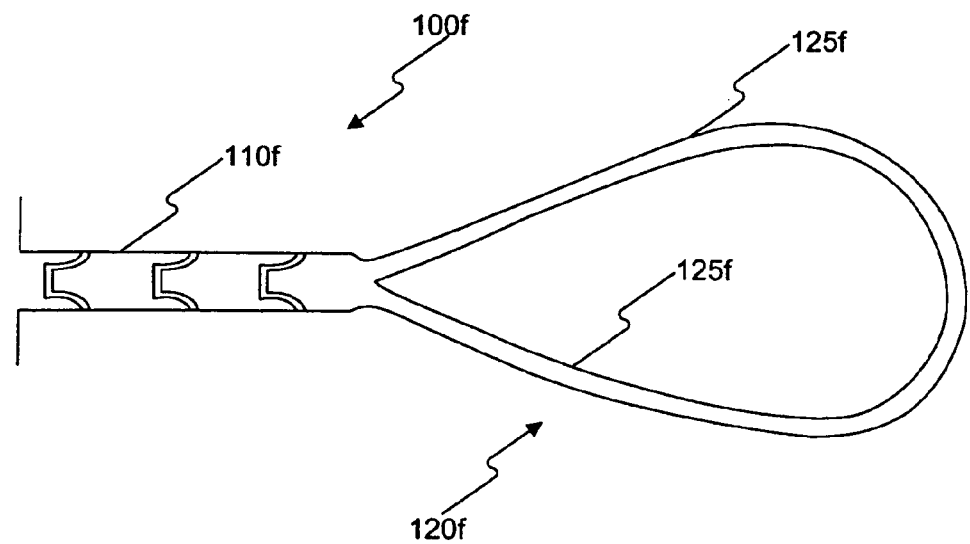
FIG. 17 is a top view of the device of FIG. 16.

As described above, a particular desired basket shape may be imparted to the legs 125f by cutting and shaping fabrication steps. FIGS. 14 and 15 show the retrieval assembly 120f in a closed state, and FIGS. 16 and 17 show the retrieval assembly 120f in an open state. In its closed state, the retrieval assembly 120f may substantially conform to the interior dimensions of the sheath 310. In its open state, however, the retrieval assembly 120f may expand along its width as illustrated in FIG. 17. Alternatively or additionally, the pair of loops comprising assembly 120f may separate radially from each other, as shown in FIG. 16.

Figure 18:
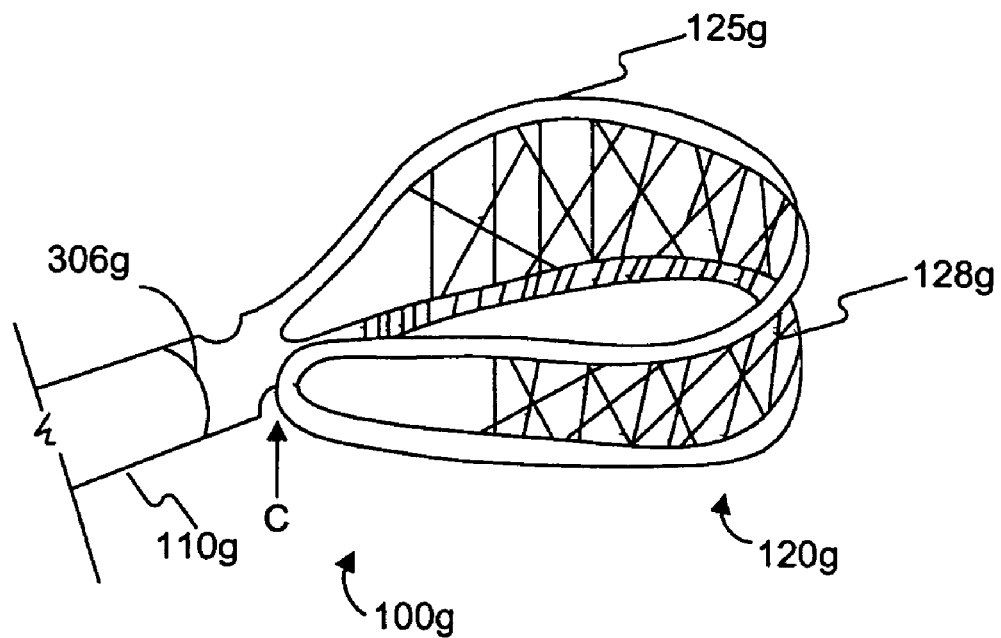
FIG. 18 is a plan view of a portion of a stone removal assistance device according to a still further embodiment of the present disclosure.

FIG. 18 shows another embodiment of a stone removal assistance device 100g. The device 100g includes a cannula 110g that defines a lumen 306g and a retrieval assembly 120g. The retrieval assembly 120g is formed by cutting a single loop from the cannula 110g. In some embodiments, the device 100g may also include a sheath (not shown).

The single loop may be formed, for example, by first cutting two loops in a portion of the cannula 110g, similar to the two loops of the device 100f shown in FIG. 13. A subsequent cut may detach one end 6f the loops from the remainder of the cannula 110g at location C, thus forming a single loop. Using the device 100f shown in FIG. 13 for illustrative purposes, cutting the cannula 110f at the location C (dashed line in FIG. 13) may detach the two loops while preserving the connection between their ends, thus forming a single, larger loop.

As shown in FIG. 18, the retrieval assembly 120g may also include netting 128g attached to the loop. Netting 128g may be any suitable, flexible, biocompatible fabric, weave, filter-like structure, cross-wire arrangement, or the like. Netting 128g may be provided throughout the entire loop or only part of the loop. The netting 128g may assist trapping stones and/or other material in the basket defined by the retrieval assembly 120g and/or may assist in acting as a backstop during laser lithotripsy.

Figure 19:
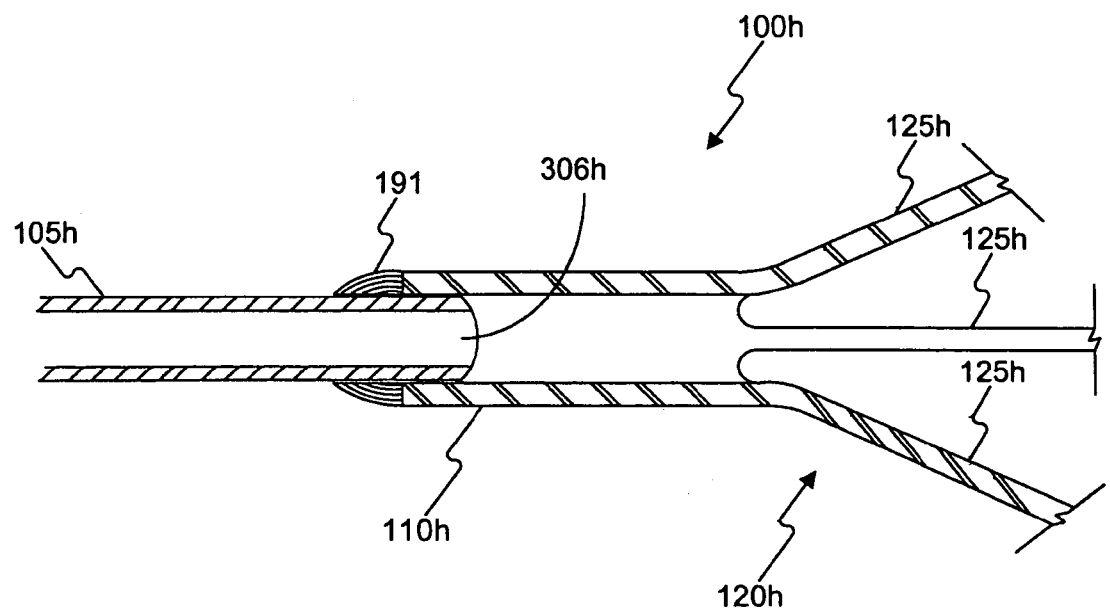
FIG. 19 is a cross-sectional view of a portion of a stone removal assistance device according to another embodiment of the present disclosure.

FIG. 19 shows a cross-section of a portion of another embodiment of a stone removal assistance device 100h. The device 100h includes an elongate member 105h, a cannula 110h, and a retrieval assembly 120h having one or more legs 125h. The cannula 110h and the one or more legs 125h of the retrieval assembly 120h may be cut from a single piece of cannula 110h.

The cannula 110h may be attached to the elongate member 105h with an attachment means 191. The attachment means 191 may be, for example, a weldment, solder, epoxy, cyanoacrylate, or brazing material. The elongate member 105h may be hollow or solid and may be, for example, a mandrel formed from wire. In an embodiment where the elongate member 105h is hollow, the elongate member 105h may define at least one lumen 306h.

Figure 20:
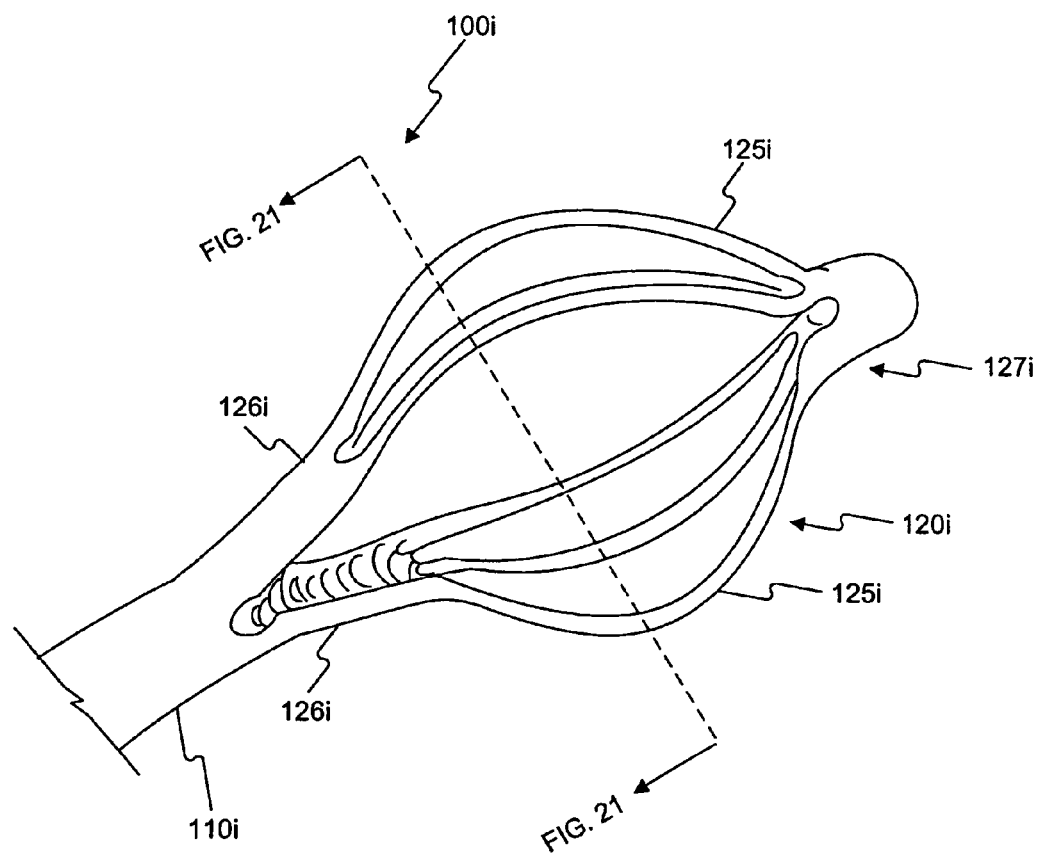
FIG. 20 is a plan view of a portion of a stone removal assistance device according to still another embodiment of the present disclosure.
Figure 21:
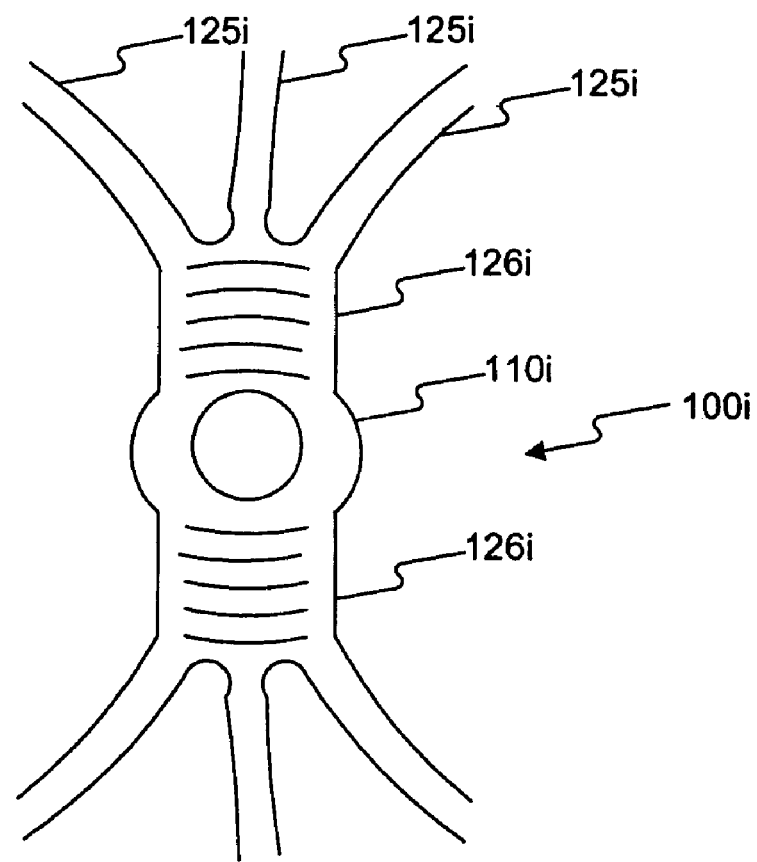
FIG. 21 is a cross-sectional view of the device of FIG. 20.

FIG. 20 illustrates a further embodiment of a device 100i according to the present disclosure. The device 100i includes a cannula 110i and a retrieval assembly 120i formed from a single piece of cannula 110i. FIG. 21 is a cross-sectional view of the device illustrated in FIG. 20, with the section indicated by the dashed line in FIG. 20.

The retrieval portion 120i includes two proximal legs 126i, six distal legs 125i, and a distal end portion 127i. The retrieval portion 120i may have a parachute-like shape and each proximal leg 126i may be integrally joined at one end with the cannula 110i, and at the other end with three of the distal legs 125i. The opposite end of each distal leg 125i may be connected to the distal end portion 127i. In some embodiments, the proximal legs 126i may be longer or shorter than the distal legs 125i, and the proximal legs 126i may be wider than the distal legs 125i. The proximal legs 126i may be made by, for example, cutting two slots completely through the cannula 110i approximately 180 degrees apart. Any number of additional cuts may be made in between these initial cuts to obtain a corresponding number of distal legs 125*i* made from the proximal legs 126*i*. Variations in the number of proximal legs 126*i* and distal legs 125*i*, as well as their lengths, widths, and other dimensional features in alternative embodiments will be apparent to one of ordinary skill in the retrieval basket arts.

When used in cooperation with a sheath (not shown), the retrieval portion 120*i* may assume various configurations to assist capture and/or release of a material or stone in a patient's body. For example, the retrieval portion 120*i* may be extended completely out of the sheath to permit a fully open state. A stone (not shown) may be captured, and the proximal legs 126*i* may be covered with the sheath to partially close the retrieval portion 120*i* to trap the stone between the distal legs 125*i*.

In embodiments of the present disclosure, including various embodiments already described above and others to be described herein, a device including, for example, a basket made of shape memory material such as wire, may be used to immobilize a stone or other like material during, for example, lithotripsy. In some embodiments, the basket of the device may form a backstop and may prevent the advancement of the stone into, for example, the ureter during lithotripsy. The backstop may also enable a user to increase the amount of energy supplied to the stone during the procedure.

Figure 9:
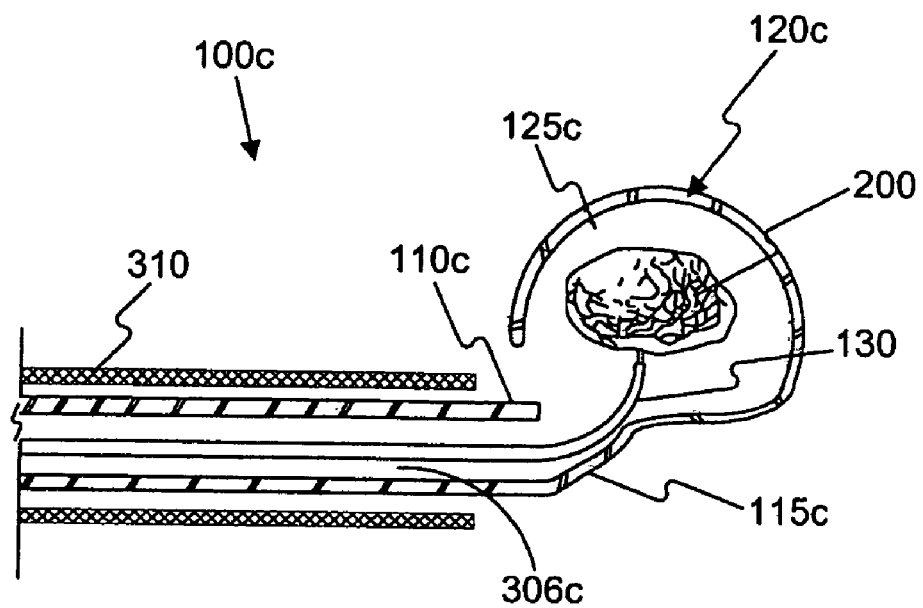
FIG. 9 is a cross-sectional view of a stone removal assistance device according to another embodiment of the present disclosure.
Figure 26:
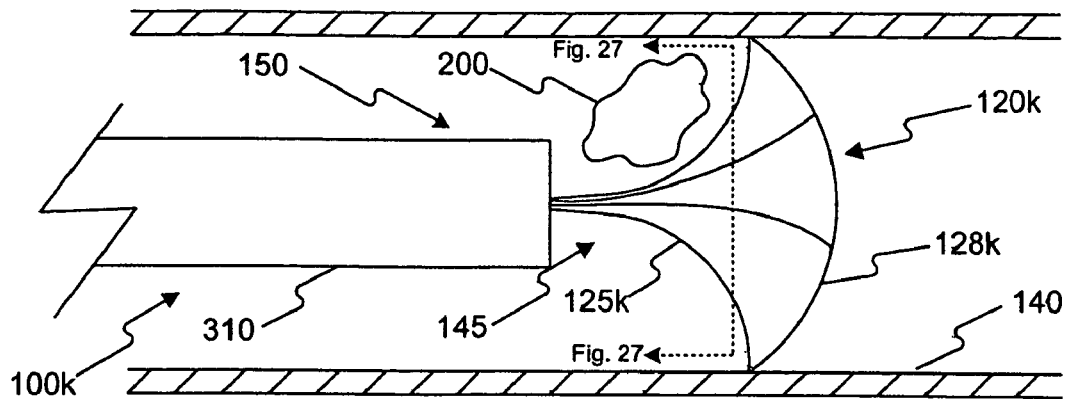
FIG. 26 is an operational view of a portion of a stone removal assistance device according to another embodiment of the present disclosure.

As illustrated in FIG. 26, a device 100*k* may be placed into position past, above, or otherwise distal to a stone 200. A lithotripsy device (not shown) may then be used to break up the stone 200. With the device 100*k* in place, stone fragments may then be swept into the bladder where they may be passed. Once the device 100*k* is in position, the basket 120*k* may be deployed by means of an actuation device such as, for example, a thumbtab (not shown) connected to a wire (not shown) that may be coaxial with an outer sheath 310 of the device 100*k*. The distal end of the coaxial wire may be attached to the proximal end 145 of the basket 120*k*. When the thumbtab is moved in the direction of the distal end 150 of the device 100*k*, the basket 120*k* may be urged out of the sheath 310 to form a backstop. FIGS. 9, 26, and 29 illustrate different embodiments of a deployed backstop within the body of a patient.

Figure 27:
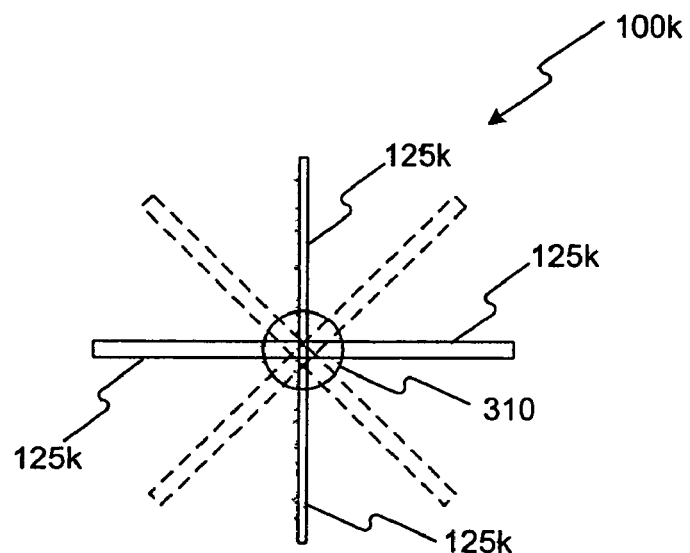
FIG. 27 is an end view of the device of FIG. 26.

As shown in FIG. 26, in one embodiment the basket 120*k* may expand distal the stone 200 to span substantially the entire passage 140 of the body in which the device 100*k* is used. Basket 120*k* of this embodiment may assume an umbrella-like or mushroom-like shape when opened. In such an embodiment, the basket 120*k* may include four legs 125*k* and in some embodiments may include as many as eight legs 125*k*. For example, FIG. 27 illustrates an end view of a four-leg embodiment of the device 100*k* of FIG. 26. In this embodiment, the legs 125*k* may be substantially evenly spaced and each leg 125*k* may be approximately 90 degrees apart from the closest adjacent leg. As illustrated by the dotted lines of FIG. 27, in an eight-legged embodiment, the legs 125*k* may also be substantially evenly spaced. Other embodiments with different numbers of legs of various spacing may be suitable. FIG. 28 shows an elevation view of an eight-legged embodiment. As shown in FIGS. 26 and 28, the basket 120*k* may include netting 128*k*. The netting 128*k* may be made of, for example, shape memory wire or any other netting, fabric, or other like material known in the art.

FIG. 29 illustrates another embodiment of a stone removal assistance device 100*l*. In this embodiment, the basket 120*l* may be made of a single piece of shape memory wire. The basket 120*l* may be substantially curled and/or spiral-shaped and may expand distal a stone 200 to span substantially the entire passage of the body 140 in which the device 100*l* is used, or less than the passage of body 140. An instrument useful in reducing the size of a stone such as, for example, a laser light component 130, may be used in conjunction with the device 100*l* and act on the stone 200 while external to the device 100*l*. Alternatively, laser light component 130 may extend through a lumen 305 of sheath 310 to reach and act on stone 200. The device 100*l* may prevent the migration of the stone 200 while the stone is acted on. FIG. 30 shows an exemplary end view of the device 100*l*. As shown in FIGS. 29 and 30, in some embodiments of the present disclosure, the tip 127*l* of the basket 120*l* may be, for example, dulled, rounded, or otherwise have an atraumatic shape or surface texture.

As described above with respect to FIG. 1, the device 100*l* may include a handle (not shown) having an actuating mechanism (not shown). Once the device 100*l* is positioned distal the stone 200, the retrieval assembly 120*l* may be deployed above the stone 200 by manipulating the actuating mechanism toward the distal end of the device 100*l* and thereby urging the retrieval assembly 120*l* at least partially beyond the lumen 305 of the sheath 310. The actuating mechanism may be operatively connected to a proximal end of an elongate member (not shown) of the device 100*l* to facilitate movement of the retrieval assembly 120*l*. The elongate member may be coaxial with the sheath 310.

Figure 31:
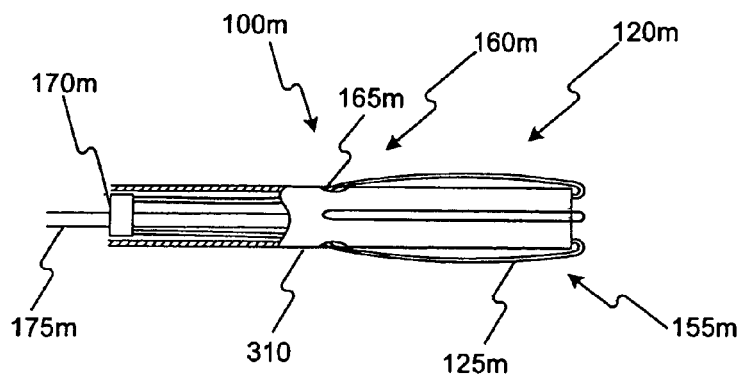
FIG. 31 is a partial cutaway view of a portion of a stone removal assistance device according to yet another embodiment of the present disclosure.
Figure 32:
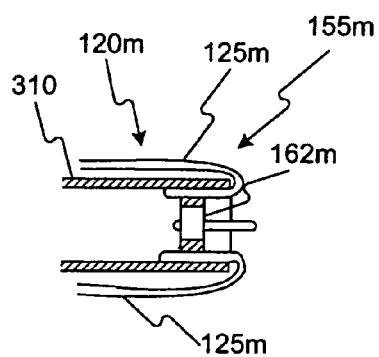
FIG. 32 is a cross-sectional view of a distal end of the device of FIG. 31.
Figure 33:
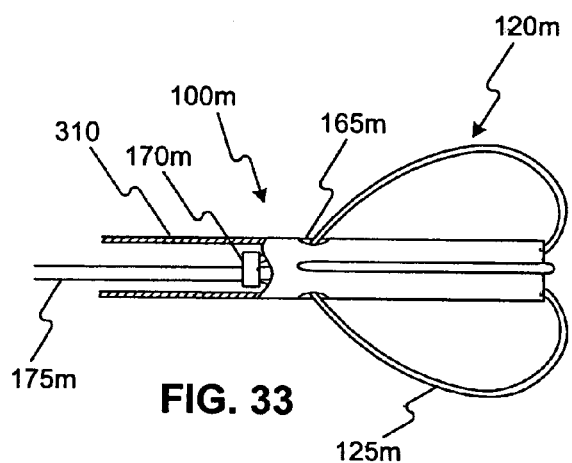
FIG. 33 is an expanded basket of the device of FIG. 31.

FIG. 31 shows another device according to an embodiment of the present disclosure that may immobilize a stone during laser lithotripsy and retrieve stone fragments after the stone reduction processes. As shown in FIG. 31, the device 100*m* may include a plurality of preformed basket legs 125*m*. The distal ends 155*m* of the basket legs 125*m* may be fixed to the distal end of the sheath 310 by any conventional attachment means known in the art such as, for example, crimping, soldering, or adhesives. FIG. 32 is a cross-sectional view of the distal end 155*m* of the device 100*m* illustrating a crimped connection. In such a connection, a crimp ring 162*m*, or other conventional crimping means, may be used to secure the legs 125*m* to the sheath 310. Although shown as attached to an inner surface of the sheath 310, in other embodiments, the legs 125*m* may be attached to an external surface of the sheath 310. In such an embodiment, the crimping ring 162*m* may be external to the sheath 310 or may be omitted. Although FIGS. 31-33 illustrate exemplary baskets 120*m* having four legs 125*m*, other embodiments of the device 100*m* may include more or less than four legs.

As shown in FIG. 31, in a closed position, the basket legs 125*m* may be located in close proximity to the outside surface of the sheath 310, and the proximal ends 160*m* of the legs 125*m* may pass through ports 165*m* located along the sheath 310 and attach to a collar 170*m* within the sheath 310. The collar 170*m* may be attached to a push rod 175*m* or any other flexible elongate member extending through the sheath 310 and translating longitudinally relative to sheath 310 for activation of the basket 120*m*. For example, in some embodiments, the push rod 175*m* may be an elongate actuation member. When the push rod 175*m* is advanced in a direction toward the distal end 155*m* of the device 100*m*, the legs 125*m* of the basket 120*m* may be urged through ports 165*m* and may expand to their preformed shape. An expanded basket 120*m* of the current embodiment is shown in FIG. 33.

Figure 34:
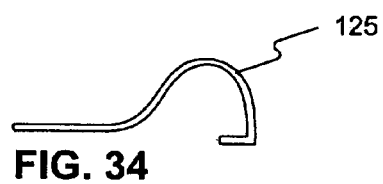
FIG. 34 is a leg for use in a stone removal assistance device.
Figure 35:
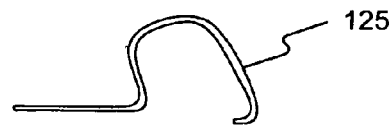
FIG. 35 is another leg for use in a stone removal assistance device.
Figure 36:
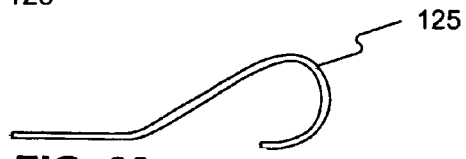
FIG. 36 is a further leg for use in a stone removal assistance device.

The legs 125*m* of the basket 120*m* may be made of any shape memory material or alloy known in the art such as, for example, stainless steel, nitinol, plastics, composites, or shape memory plastics. In addition, the legs 125*m* may be of any preformed shape or configuration known in the art such as, for example, substantially semicircular (FIG. 34), substantially semiovular (FIG. 35), or substantially semiheart-shaped (FIG. 36).

Figure 37:
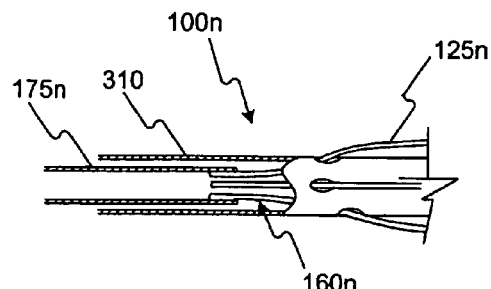
FIG. 37 is a partial cutaway view of a portion of a stone removal assistance device according to a further embodiment of the present disclosure.

As shown in FIG. 37, in another embodiment the push rod 175n may be a hollow tube that is coaxial with the sheath 310. The proximal end 160n of each of the legs 125n may be connected to the push rod 175n by any connection means known in the art. For example, in some embodiments, the proximal end 160n of the legs 125n may be welded, soldered, crimped, or otherwise fixed to the push rod 175n. As in the device 100m of FIG. 31, the distal end (not shown) of the legs 125n may be connected to the distal end of the sheath 310.

Figure 38:
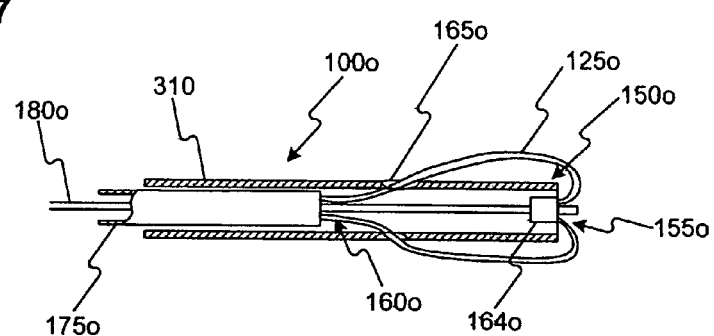
FIG. 38 is a cross-sectional view of a portion of a stone removal assistance device according to a still further embodiment of the present disclosure.

As shown in FIG. 38, a central stabilizing rod 180o may be disposed within a hollow push rod 175o and may extend substantially the length of the device 100o. The push rod 175o and the stabilizing rod 180o may be made of any materials known in the art. The push rod 175o may be, for example, a flexible metal wire. The push rod 175o may be moveable independent of the stabilizing rod 180o within the sheath 310 of the device 100o, such as the distal end of sheath 310. The stabilizing rod 180o may be fixed to at least a portion of the device 100 or, alternatively, may be unattached to the device 100o.

As shown in FIG. 38, a proximal end 160o of each of the legs 125o may be fixed to the distal end of the push rod 175o. Although FIG. 38 shows the legs 125o as attached to an inner surface of the push rod 175o, in other embodiments, the legs 125o may be fixed to an outer surface of the push rod 175o. The legs 125o may be fixed thereto by any conventional means known in the art such as, for example, welding, soldering, crimping, or adhering. In this embodiment, the distal ends 155o of the basket legs 125o may be attached to the distal end of the stabilizing rod 180o. In some embodiments, a connector 164o may connect the legs 125o to the stabilizing rod 180o. The connector 164o may be any conventional junction means, such as a crimp ring.

As in the embodiments described above, the legs 125o may be deployed by advancing the push rod 175o toward the distal end 150o of the device 100o. In the embodiment of FIG. 38, the sheath 310 may be omitted. Alternatively, the sheath 310 may include a number of ports 165o and at least a portion of the legs 125o may pass through the ports 165o as the push rod 175o is advanced toward the distal end 150o of the device 100o.

Figure 39:
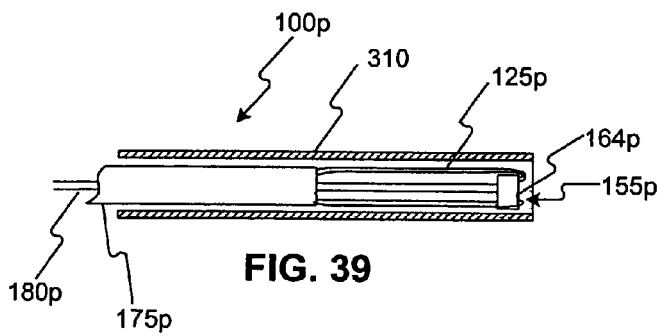
FIG. 39 is a cross-sectional view of a portion of a stone removal assistance device according to another embodiment of the present disclosure.
Figure 40:
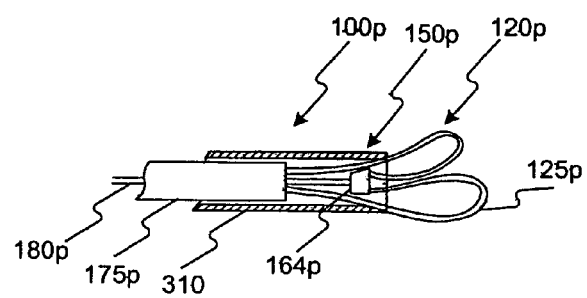
FIG. 40 is a cross-sectional view of the device of FIG. 39.

In yet another exemplary embodiment, the basket legs 125p of a device 100p may be entirely within the sheath 310 when the basket is in its collapsed position, and the ports located along the sheath 310 may be omitted, as shown in FIG. 39. In this embodiment, at least a portion of the legs 125p may extend from the distal end of the sheath 310 as the push rod 175p is advanced. The distal ends 155p of the legs 125p may be connected to the stabilizing rod 180p by a connector 164p as described above. FIG. 40 illustrates a partially expanded basket 120p of the device 100p.

Figure 41:
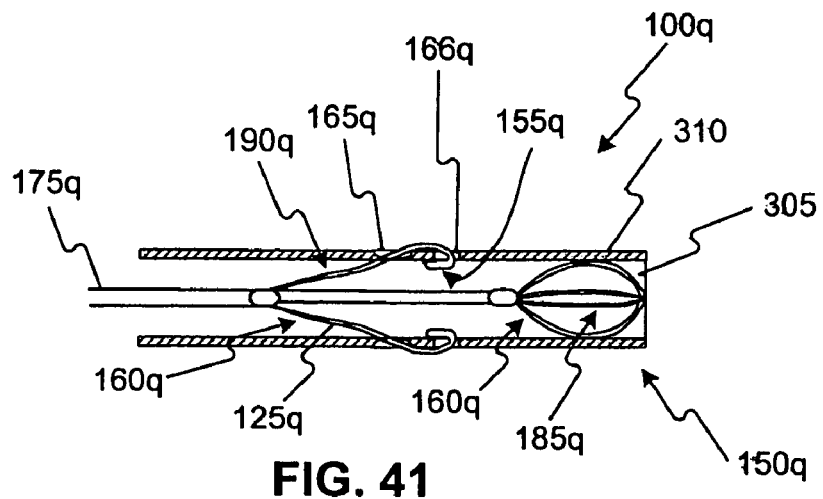
FIG. 41 is a cross-sectional view of a portion of a stone removal assistance device according to yet another embodiment of the present disclosure.
Figure 42:
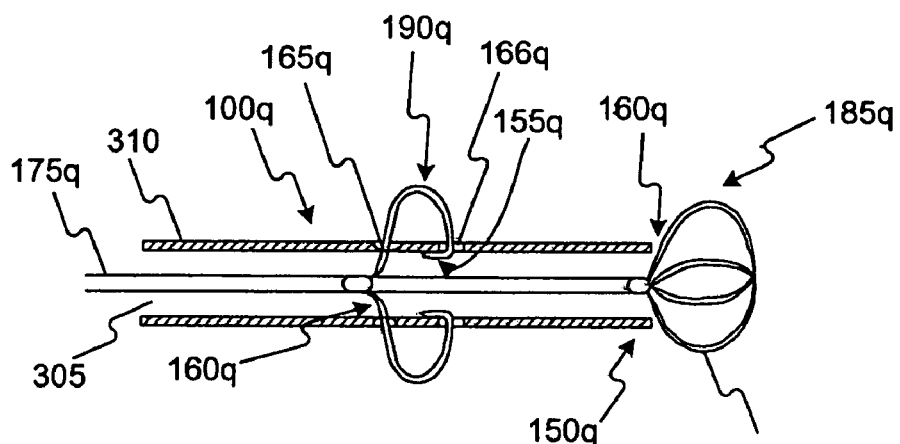
FIG. 42 is a cross-sectional view of the device of FIG. 41.

Moreover, as illustrated in FIGS. 41-45, in some embodiments of the present disclosure, the device may include more than one basket for immobilizing and/or capturing a stone. For example, as shown in FIGS. 41 and 42, a multibasket device 100q may include a distal basket 185q and a proximal basket 190q. The distal basket 185q may be collapsed when withdrawn within a lumen 305 of the sheath 310 (FIG. 41) and may be expanded when extended at least partially outside of the lumen 305 of the sheath 310 (FIG. 42). The proximal end 160q of the legs 125q of the distal basket 185q may be fixed to the distal end of the push rod 175q. The distal basket 185q may be expanded (FIG. 42) or collapsed (FIG. 41) by actuating the push rod 175q toward the distal or proximal end of the device 100q relative to sheath 310, respectively. The distal basket 185q may include at least two legs 125q, and as shown in FIGS. 41 and 42, in some embodiments, the distal basket 185q may include four legs 125q, each connected at their proximal end to the distal end of the push rod 175q. Each of the legs 125q of the distal basket 185q may be made of, for example, shape memory material.

Figure 43:
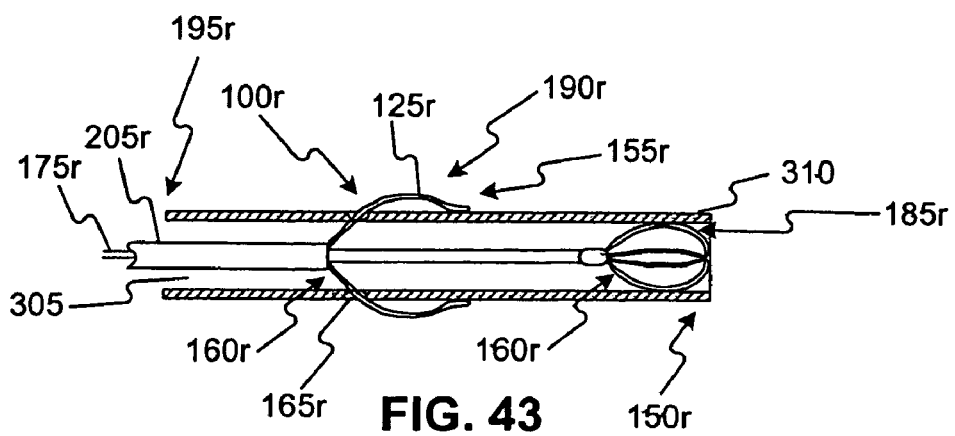
FIG. 43 is a cross-sectional view of a portion of a stone removal assistance device according to still another embodiment of the present disclosure.

The proximal basket 190q may also include at least two legs 125q. The distal end 155q of each leg 125q of the proximal basket 190q may be fixedly attached to the sheath 310. Although FIGS. 41 and 42 illustrate the legs 125q of the proximal basket 190q being connected to an inner surface of the sheath 310, in other embodiments, the legs 125q may be connected to an outer surface of the sheath 310 (FIG. 43). In an embodiment where the legs 125q of the proximal basket 190q are connected to an inner surface of the sheath 310 (FIGS. 41 and 42), the sheath may include a number of proximal ports 165q and distal ports 166q. In such an embodiment, at least a portion of each leg 125q may be disposed within a corresponding proximal port 165q and a different portion of each leg 125q may be disposed within a corresponding distal port 166q. At least a portion of the legs 125q may extend and retract through the proximal ports 165 as the proximal basket 190q is opened and closed, respectively. In embodiments where the legs 125q of the proximal basket 190q are connected to an outer surface of the sheath 310 (FIG. 43), the distal ports 166q may be omitted. As described above, the legs 125q may be fixed to the sheath 310 by any conventional means such as, for example, welding, soldering, crimping, or adhering.

The proximal end 160q of the proximal basket legs 125q may be fixed to the push rod 175q by the same or similar conventional means. As shown in FIG. 42, to expand the proximal basket 190q, the push rod 175q may be advanced toward the distal end 150q of the device 100q relative to sheath 310. Advancing the push rod 175q in this direction may also at least partially expand the distal basket 185q as basket 185q exits the distal end of sheath 310. Because at least a portion of each basket 185q, 190q is attached to the push rod 175q, the baskets 185q, 190q may be expanded and collapsed substantially in unison by advancing and withdrawing the push rod 175q, respectively. In an embodiment in which the baskets 190q, 185q are expanded within, for example, the urinary tract of a patient, the device 100q may be capable of immobilizing a stone both distally and proximally. To do so, the device 100q in the undeployed state shown in FIG. 41 may be advanced until the distal end of the sheath 310 is distal the stone. The distal basket 185q and the proximal basket 190q may then be expanded by urging the push rod 175q in the distal direction and thereby trapping the stone between the two expanded baskets 185q, 190q.

Figure 44:
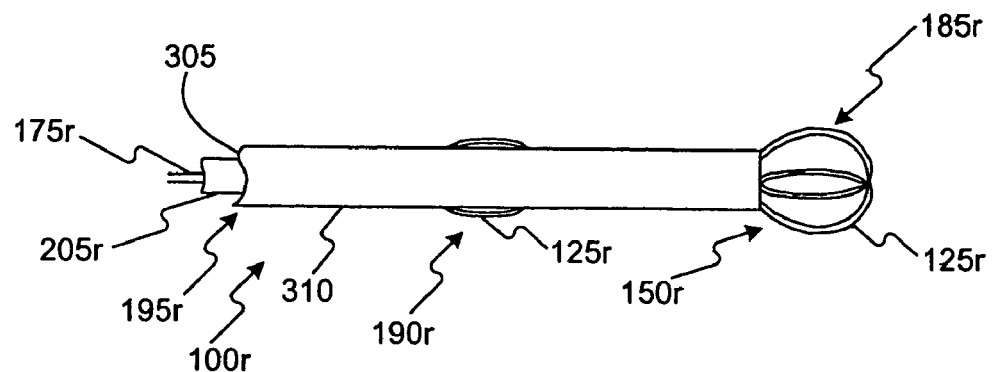
FIG. 44 is a side view of the device of FIG. 43.
Figure 45:
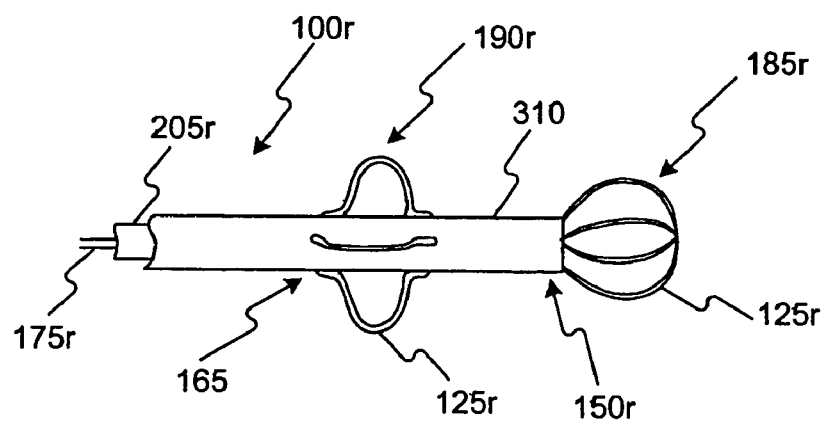
FIG. 45 is a further side view of the device of FIG. 43.

In other embodiments, the proximal and distal baskets may be individually expandable and collapsible. For example, as shown in FIGS. 43-45, a multibasket device 100r may include a proximal basket 190r and a distal basket 185r. The proximal end 160r of the legs 125r of the distal basket 185r may be connected to a push rod 175r disposed within a lumen 305 of the sheath 310. This connection may be facilitated by any of the connection means discussed above. Advancing the push rod 175r toward the distal end 150r of the device 100r relative to sheath 310 may urge the distal basket 185r out from within the lumen 305 of the sheath 310, thereby at least partially expanding the distal basket 185r. Moving the push rod 175r in a direction toward the proximal end 195r of the device 100r relative to sheath 310 may withdraw the distal basket 185r into the lumen 305 and may at least partially collapse the distal basket 185r. An exemplary collapsed position of the distal basket 185r is illustrated in FIG. 43 and an exemplary expanded position of the basket 185r is shown in FIGS. 44 and 45.

In this same embodiment, the proximal basket 190r may include at least two legs 125r. A distal end 155r of each leg 125r may be fixedly attached to the outer surface of the sheath 310, as shown in FIG. 43, or attached to an inner surface of sheath 310, like that shown in FIGS. 41 and 42. A proximal end 160r of each leg 125r may be fixedly attached to a hollow tube 205r disposed within the lumen 305 of the sheath 310. The hollow tube 205r may be an extending member or any other like device known in the art. These connections may be facilitated by any of the connection means discussed above. In some embodiments, the push rod 175r may be disposed within the tube 205r such that the push rod 175r and the tube 205r are independently moveable. The tube 205r may be made of any material known in the art and may be rigid enough to assist in expanding and collapsing the proximal basket 190r within, for example, the urinary tract of a patient, yet flexible enough to traverse the anatomy. These materials may be similar to or the same as the materials of the push rod 175r. As shown in FIG. 44, in a collapsed position, at least a portion of the legs 125r of the proximal basket 190r may extend substantially along the outer surface of the sheath 310 and at least a portion of the legs 125r may be disposed within the lumen 305. As the tube 205r is advanced toward the distal end 150r of the device 100r, a portion of the legs 125r may exit the lumen 305 through one or more ports 165 defined by the sheath 310, as shown in FIG. 45.

Figure 46:
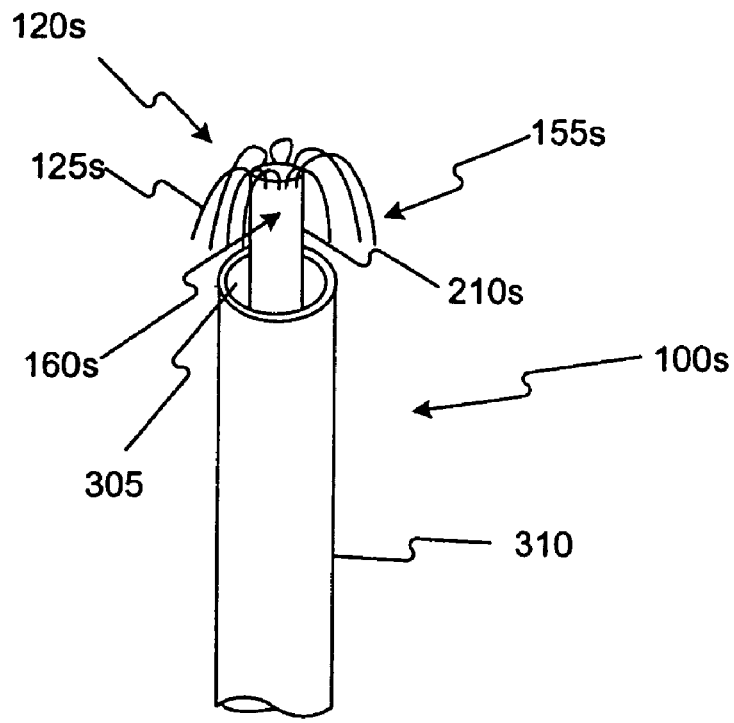
FIG. 46 is a partial view of a stone removal assistance device according to an additional embodiment of the present disclosure.
Figure 47:
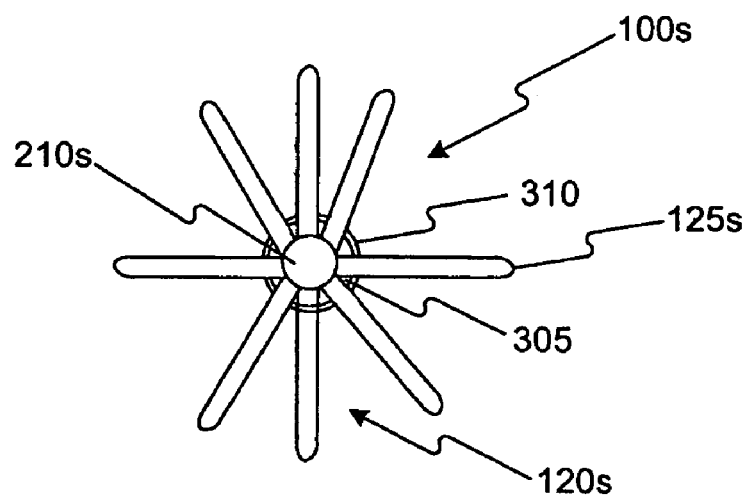
FIG. 47 is a top view of the device of FIG. 46.

Another embodiment of a device of the present disclosure useful in, for example, repositioning, removing, and/or preventing the migration of stones or other foreign matter within the body of a patient is shown in FIGS. 46-47. Device 100s may include at least three wires 125s fixedly attached to a distal end of a shaft 210s. The wires 125s may be substantially flexible and may be made from any material known in the art such as, for example, stainless steel, nitinol, or a combination thereof. The shaft 210s may be substantially flexible, but may be rigid enough to urge the wires 125s out from a distal end of a sheath 310 when the device 100s is disposed within a tightly constrained area within the body of the patient. The shaft 210s may be made from materials similar to or the same as the wires 125s. The sheath 310 may be substantially flexible, substantially hollow, and may define at least one lumen 305. The sheath 310 may be formed from any suitable biocompatible material known in the art, such as those mentioned above. The sheath 310 may also be a metal coated with a polymer. The sheath 310 of the present embodiment may have an outer diameter in the range of approximately 0.013 inches to approximately 1.00 inches, and the corresponding device length may be in the range of approximately 50 centimeters to approximately 200 centimeters.

As shown in FIG. 47, the wires 125s may be spaced substantially evenly about the shaft 210s and may have any cross-sectional shape known in the art such as, for example, triangular, circular, square, rectangular, or trapezoidal. Each wire 125s may have the same cross-sectional shape, or each wire 125s may have a different shape depending on the requirements of the application. The proximal ends 160s of the wires 125s may be connected to the distal end of the shaft 210s by any of the conventional attachment means discussed above. Alternatively, in some embodiments, the wires 125s may be formed from the shaft 210s itself. In such embodiments, the wires 125s may be formed by chemically etching, laser cutting, mechanically cutting, or otherwise modifying the shaft 210s. As a result of being formed from the shaft 210s, the wires 125s may have a cross-section that substantially corresponds to a portion of a cross-section of the shaft 210s. Regardless of whether the wires 125s are connected to or formed from the shaft 210s, each wire 125s may have a free distal end 155s, as shown in FIG. 46.

When the shaft 210s is disposed substantially within a lumen 305 of the sheath 310, the wires 125s may also be disposed therein in a substantially straight, collapsed position. As the shaft 210s is moved toward the distal end of the sheath 310, at least a portion of the wires 125s may exit the distal end of the sheath 310. In some embodiments of the present disclosure, the wires 125s may be formed of shape memory material such that upon at least partially exiting the sheath 310, the wires 125s may form a basket having any desirable shape known in the art. For example, as illustrated in FIG. 46, the wires 125s may form a substantially umbrella-shaped basket 120s. As viewed from the distal end of the shaft 210s (FIG. 47), a fully open basket 120s in this configuration may have a diameter in the range of approximately 0.026 inches to approximately 2.00 inches. The corresponding wires 125s of such a basket 120s may have a length in the range of approximately 0.013 inches to approximately 1.00 inches.

When the wires 125s are urged from the distal end of the sheath 310, the basket 120s may substantially conform to the diameter of the body passage in which the device 100s is disposed. The device 100s may be positioned, and the basket 120s. may be expanded, distal a stone to limit the stone's mobility during stone reduction and/or removal procedures such as, for example, laser lithotripsy. The device 100s may also be used to sweep a stone out from within the body of the patient. The unattached distal ends 155s of the wires 125s may be rounded, bent, folded, dulled, or otherwise shaped so as not to cause trauma to the body of the patient during use.

Figure 48:
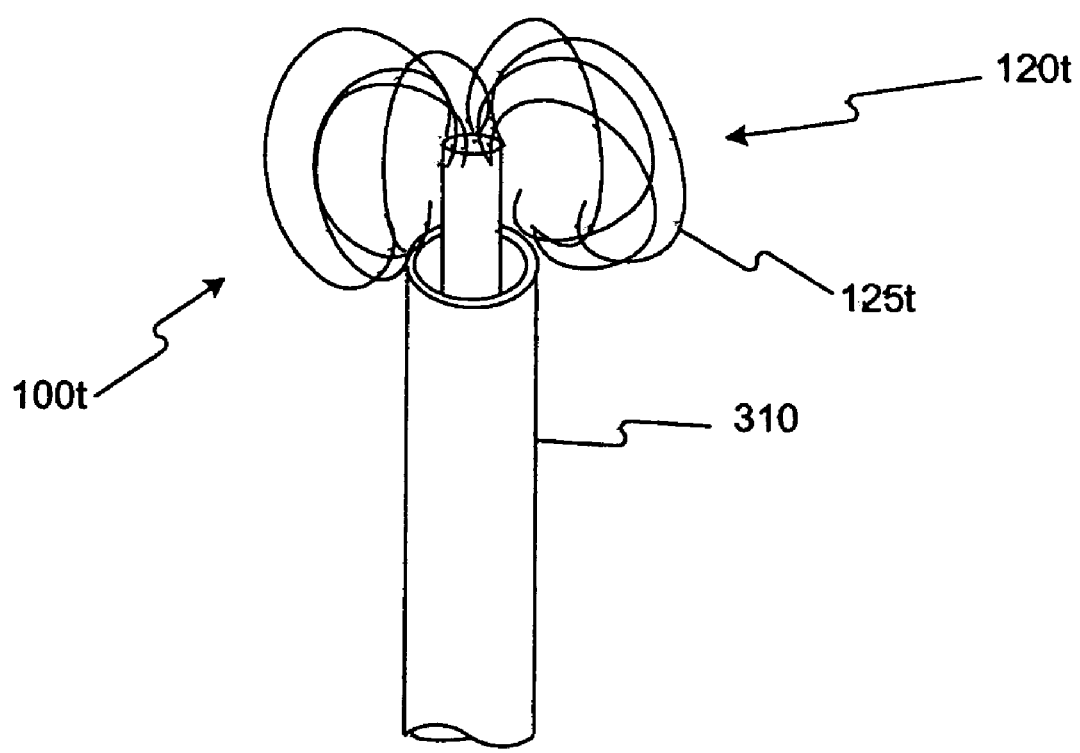
FIG. 48 is a partial view of a stone removal assistance device according to another embodiment of the present disclosure.

As shown in FIG. 48, in another embodiment, the basket 120t may include legs that are substantially round or circular in an expanded, deployed position. The basket 120t may be expanded by manipulating the sheath 310 of the device 100t in a proximal direction. As the sheath 310 is retracted, the wires 125t may curl backwards in the proximal direction, thereby expanding the basket 120t. The expanded basket 120t may be useful in isolating, manipulating, and/or removing stones from the body of the patient. The basket 120t may be collapsed by manipulating the sheath 310 in the distal direction. As the sheath 310 passes over the wires 125t, the sheath 310 may force the wires 125t to straighten to facilitate entrance into a distal end of the sheath 310.

Like embodiments described above, other embodiments of the present disclosure relate to devices that include an end effector, such as a basket or snare, made from a single piece of tube or cannula. Such configurations may eliminate the need to join separate wires at the base and/or tip of the end effector with weldments, crimped sections, soldered sections, over-cannulas, or other conventional means and may, thus, reduce the overall size of the device. Although not shown in FIGS. 49-52, such devices may include a sheath to facilitate the opening and closing of the basket.

Also like other embodiments discussed throughout this disclosure, such embodiments of devices may be particularly useful in, for example, capturing, immobilizing, removing, and/or reducing the size of gallstones or other like foreign objects and may include a basket having any number of legs useful in, for example, isolating, manipulating, removing, or reducing the size of a stone. In certain embodiments of the present disclosure, the device may be a cautery device useful in, for example, cauterizing and/or removing cessile or low-profile polyps or other like biological material.

Figure 49:
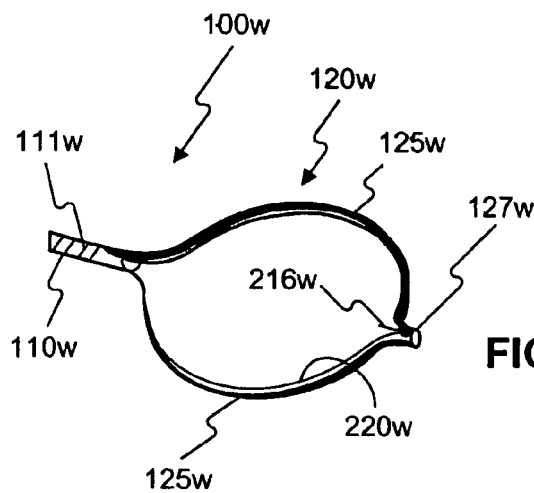
FIG. 49 is a plan view of a portion of a stone removal assistance device according to still another embodiment of the present disclosure.
Figure 50:
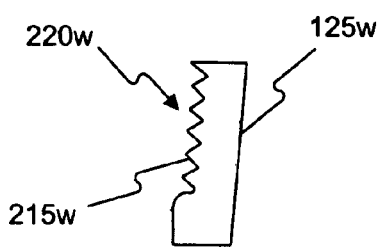
FIG. 50 is a cutaway view of the device of FIG. 49.

As illustrated in FIG. 49, a basket 120w may include a continuous loop defined by two legs 125w and a distal end 127w. Basket 120w, therefore, is shaped like a snare device.

The legs 125w of the loop may be formed by, for example, laser cutting at least a portion of the cannula 110w. The width, shape, and corresponding mechanical characteristics of the legs 125w may be determined by at least the size and configuration of these cuts. Although the embodiments shown in FIGS. 49-52 illustrate legs 125w formed through substantially longitudinal cuts, in other embodiments, the legs may be formed by laser cutting the cannula in any advantageous configuration. For example, in some embodiments, the legs may be formed by cutting the cannula in a substantially spiral configuration. Such cuts may result in a substantially helical basket (not shown).

The legs 125w may further include one or more contact features 215w (FIG. 50) located on an inner surface 220w of each leg 125w. The contact features 215w may improve the ability of each leg 125w to grip and/or reduce the size of a stone, polyp, or other object within the body of the patient and may be, for example, teeth, serrations, spikes, or any other conventional geometry useful in aiding in lithotripsy by grasping a stone. In some embodiments, the contact features 215w may be formed of at least one layer of the cannula 110w by laser cutting and/or chemically etching the inner surface 220w of the legs 125w.

In other embodiments, at least one contact feature 215w may be connected to an inner surface 220w of one or more of the legs 125w, for example, at the distal tip 127w (FIG. 49) of the basket 120w. The contact feature 215w may be connected to the inner surface 220w by, for example, soldering, welding, or any other conventional means. In an embodiment, the contact feature 215w may be a spike 216w, as shown in FIG. 49. The spike 216w can aid in immobilizing a stone during lithoptripsy.

Figure 51:
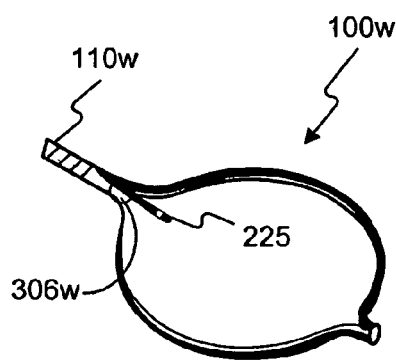
FIG. 51 is an additional plan view of the device of FIG. 49.

The cannula 110w may be made from any of the material mentioned above, and the mechanical characteristics of the legs may also result from the cannula material. For example, the cannula 110w may be made from Elgiloy, stainless steel (400 series), nitinol, or a combination thereof. In some embodiments, the cannula 110w may be a multilayered cannula consisting of, for example, an inner layer of nitinol and an outer layer of stainless steel. Such multilayered cannulas may increase the strength, dilation force, and overall stone reduction and/or removal capabilities of the device 100w. As illustrated in FIG. 51, the cannula 110w may also be hollow and may define at least one lumen 306w. The lumen 306w may be useful in delivering fluid to and/or removing fluid from a treatment site within the body of the patient, such as a location within the body of the patient in the vicinity of a stone, polyp, or other like object. The lumen 306w may also be sized and shaped to accept a guidewire (not shown). Thus, in some embodiments, the device may be passed over a guidewire to a treatment site.

As shown in FIG. 51, the lumen 306w may be sized and shaped to accept, for example, a therapeutic or diagnostic device 225, such as an electrohemostasis catheter, an injection needle, or other like device. An injection needle may be capable of injecting, for example, saline or other like substances into a polyp to raise the polyp for rapid snaring with the device 100w.

Referring again to FIG. 49, a section of the cannula 110w may include one or more flexibility features 111w, The flexibility features 111w may be positioned in any location along the cannula 110w to assist in improving the flexibility of the device 100w during cannulation. The flexibility features 111w may be, for example, spiral, helical, triangular, D-shaped, dove-tail shaped, or any other shape known in the art, and may be, for example, laser cut into at least one layer of the cannula 110w.

Figure 52:
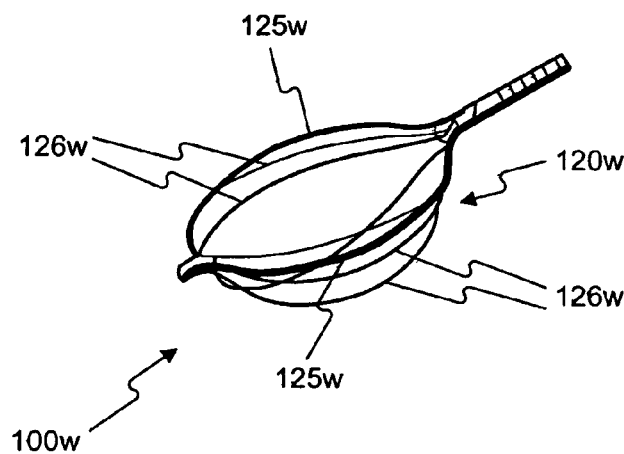
FIG. 52 is a plan view of a portion of a stone removal assistance device according to another embodiment of the present disclosure.

Basket 125w may be connected to a source of cautery current and used as an electrocautery device to remove, for example, a polyp or other tissue, similar to a snare device. In addition, as shown in FIG. 52, the basket 120w may include at least two legs 125w and may include any number of additional legs 126w useful in, for example, capturing a polyp after cauterization. The additional legs 126w may be formed by laser cutting cannula 110w and/or at least one of the legs 125w of the basket 120w and may form, for example, a net or scoop-type geometry.

The devices described above may be used, for example, in urological procedures to, for example, remove stones, polyps, or other materials from anywhere in the urinary system. The devices include baskets having distal ends that are more flexible and/or less likely to cause damage as compared to the distal ends of some prior devices. The baskets of the present disclosure may be quickly manufactured by, for example, preparing a precut, preformed component from a single piece of material, which is then attached to a mandrel wire.

Other embodiments of devices that incorporate principles of the present disclosure will be apparent to one having ordinary skill in the surgical retrieval device arts. It is intended that the specification and examples be considered as exemplary only, with a true scope and spirit of the invention being indicated by the following claims.

APPENDIX

| | | | |
|---|---|---|---|
| 5,370,657 | 6,520,968 | 20020026203 | 20050055033 |
| 5,376,094 | 6,527,781 | 20020077631 | 20050055034 |
| 5,496,330 | 6,529,756 | 20020087044 | 20050065614 |
| 5,658,296 | 6,540,657 | 20020119116 | 20050067327 |
| 5,788,710 | 6,544,227 | 20020147391 | 20050085846 |
| 5,792,145 | 6,571,686 | 20020151928 | 20050096668 |
| 5,814,064 | 6,610,056 | 20020165557 | 20050101986 |
| 5,827,324 | 6,615,071 | 20030028114 | 20050103689 |
| 5,944,728 | 6,626,915 | 20030069646 | 20050119668 |
| 5,954,661 | 6,640,120 | 20030078494 | 20050125004 |
| 6,001,118 | 6,645,199 | 20030078593 | 20050154378 |
| 6,007,546 | 6,647,281 | 20030083692 | 20050159773 |
| 6,027,508 | 6,663,594 | 20030083693 | 20050182439 |
| 6,027,509 | 6,673,080 | 20030105472 | 20050216031 |
| 6,063,082 | 6,676,682 | 20030120281 | 20050226770 |
| 6,088,614 | 6,695,834 | 20030130685 | 20050228487 |
| 6,096,053 | 6,748,953 | 20030130686 | 20050228488 |
| 6,099,534 | 6,752,811 | 20030130687 | 20050240261 |
| 6,102,920 | 6,763,261 | 20030130688 | 20050251151 |
| 6,159,219 | 6,769,550 | 20030135233 | 20050251197 |
| 6,159,220 | 6,780,193 | 20030136710 | 20050261706 |
| 6,162,179 | 6,800,080 | 20030171691 | 20050277949 |
| 6,165,200 | 6,814,740 | 20030176778 | 20060009785 |
| 6,168,603 | 6,872,211 | 20030187475 | 20060009786 |
| 6,174,318 | 6,878,151 | 20030195464 | 20060036234 |
| 6,183,482 | 6,893,431 | 20030217905 | 20060058813 |
| 6,217,589 | 6,895,267 | 20030236455 | 20060074437 |
| 6,221,039 | 6,904,303 | 20030236536 | 20060100641 |
| 6,224,612 | 6,939,353 | 20040064067 | 20060106281 |
| 6,235,044 | 7,018,385 | 20040068271 | 20060116692 |
| 6,245,089 | 7,041,117 | 20040078044 | 20060161174 |
| 6,280,451 | 7,063,707 | 20040093016 | 20060190007 |
| 6,302,895 | 7,077,849 | 20040106944 | 20060195118 |
| 6,309,399 | 7,169,154 | 20040116941 | 20060241704 |
| 6,325,807 | 7,179,269 | 20040138677 | 20070066985 |
| 6,331,183 | 7,184,811 | 20040138693 | 20070106324 |
| 6,348,056 | 7,211,089 | 20040199200 | 20070135820 |
| 6,350,266 | 7,285,117 | 20040199201 | 20070179517 |
| 6,368,328 | 7,316,692 | 20040215212 | 20070185520 |
| 6,383,196 | 7,322,989 | 20040225299 | 20070288037 |
| 6,402,761 | 7,354,455 | 20050027247 | 20070299456 |
| 6,482,162 | 20010001315 | 20050035033 | 20080058834 |
| 6,482,203 | 20010034529 | 20050038447 | 11/812,096 |
| 6,491,698 | 20010044632 | 20050053662 | 12/003,963 |

What is claimed is:

1. A medical device, comprising:
an elongate member including a longitudinal axis; and
a retrieval assembly extending distally from the elongate member, wherein the retrieval assembly and the elongate member are a continuous piece of a single material,
the retrieval assembly further comprising a distalmost end and a leg including a free distal end, the leg configured to transition from a substantially straight configuration when the retrieval assembly is in a collapsed state to a substantially curled configuration when the retrieval assembly is in an expanded state,
wherein, in the substantially straight configuration, the free distal end terminates at the distalmost end of the retrieval assembly,
wherein, in the substantially curled configuration, the free distal end is proximal the distalmost end of the retrieval assembly, and the leg defines a substantially enclosed area, and
wherein, in the substantially curled configuration, the leg intersects the longitudinal axis of the elongate member and defines a bend having a point directed towards the substantially enclosed area.

2. The device of claim 1, wherein the same piece of material is a hollow tube.

3. The device of claim 2, further comprising an optical fiber extending through a lumen defined by the tube.

4. The device of claim 3, wherein the bend is configured to assist in positioning the optical fiber towards the substantially enclosed area.

5. The device of claim 1, further comprising a sheath configured to receive the retrieval assembly and including a plurality of separate cutouts formed therein to alter the flexibility of the sheath, wherein the sheath further defines a lumen, the retrieval assembly having the collapsed state in which the retrieval assembly is substantially disposed within the lumen of the sheath, and the expanded state in which the retrieval assembly is substantially outside of the lumen of the sheath.

6. The device of claim 5, wherein the at least one cutout defines a shape to interlock neighboring portions of the sheath.

7. The device of claim 1, wherein the leg is configured to contact a biologic or foreign material in the substantially curled configuration to assist in removing the biologic or foreign material.

8. The device of claim 1, wherein the elongate member defines at least one lumen.

9. The device of claim 8, further including an optical fiber disposed within the at least one lumen of the elongate member.

10. The device of claim 1, wherein at least a portion of a proximal portion of the elongate member is removed to define corresponding interlocking portions.

11. The device of claim 1, wherein a portion of the leg distal to the bend is substantially parallel to the longitudinal axis of the elongate member.

12. The device of claim 1, wherein the leg extends across the longitudinal axis of the elongate member to a ramp portion defining the point.

13. The device of claim 1, wherein, in the substantially curled configuration, a portion of the leg distal to the bend is substantially parallel to the longitudinal axis of the elongate member.

14. The device of claim 1, wherein the leg defines a single path from the elongate member to the free distal end, and wherein the free distal end is unconnected to another leg.

15. A medical device, comprising:
an elongate member including a longitudinal axis; and
a retrieval assembly extending distally from the elongate member,
the retrieval assembly comprising a distalmost end and a leg including a free distal end, the leg configured to transition from a substantially straight configuration when the retrieval assembly is in a collapsed state to a substantially curled configuration when the retrieval assembly is in an expanded state,
wherein, in the substantially straight configuration, the free distal end terminates at the distalmost end of the retrieval assembly,
wherein, in the substantially curled configuration, the free distal end is proximal the distalmost end of the retrieval assembly, and the leg defines a substantially enclosed area, and
wherein, in the substantially curled configuration, the leg intersects the longitudinal axis of the elongate member and defines a bend greater than 90 degrees and having a point directed towards the substantially enclosed area.

16. The device of claim 15, wherein the leg is curled back and extends towards a proximal end of the device when in the substantially curled configuration.

17. The device of claim 15, wherein the leg is at least partially formed by one of cold working and hot working.

18. The device of claim 15, further including a sheath defining a lumen, the elongate member being at least partially disposed within the lumen, and the sheath being configured to assist in transitioning the retrieval assembly between the collapsed state and the expanded state.

19. The device of claim 15, wherein, in the substantially curled configuration, the distalmost end of the retrieval assembly is an intermediate portion of the leg.

20. The device of claim 15, wherein a portion of the leg distal to the bend is substantially parallel to the longitudinal axis of the elongate member.

21. The device of claim 15, wherein the elongate member includes a lumen, and wherein the bend is configured to position a medical device exiting the lumen towards the substantially enclosed area.

22. A medical device, comprising:
an elongate member including a longitudinal axis; and
a retrieval assembly extending distally from the elongate member, wherein the retrieval assembly and the elongate member are a continuous piece of a single material,
the retrieval assembly further comprising a distalmost end and a leg including a free distal end and a proximal end at the distal end of the elongate member, the leg configured to transition from a substantially straight configuration when the retrieval assembly is in a collapsed state to a substantially curled configuration when the retrieval assembly is in an expanded state,
wherein, in the substantially straight configuration, the free distal end terminates at the distalmost end of the retrieval assembly,
wherein, in the substantially curled configuration, the free distal end is proximal the distalmost end of the retrieval assembly, and the leg defines a substantially enclosed area, and
wherein, in sequential order along the leg from the a proximal end to the free distal end in the substantially curled configuration, the leg intersects the longitudinal axis of the elongate member, defines a bend having a point directed towards the substantially enclosed area, and reaches the distalmost end of the retrieval assembly.

23. The device of claim 22, wherein the retrieval assembly defines a width perpendicular to a longitudinal axis of the device and the retrieval assembly is configured to expand along its width when transitioning from the collapsed state to the expanded state.

24. The device of claim 22, wherein a portion of the leg distal to the bend is substantially parallel to the longitudinal axis of the elongate member.

25. The device of claim 22, wherein the elongate member includes a lumen, and wherein the bend is configured to position a medical device exiting the lumen towards the substantially enclosed area.

\* \* \* \* \*

UNITED STATES PATENT AND TRADEMARK OFFICE
CERTIFICATE OF CORRECTION

| | | |
|---|---|---|
| PATENT NO. | : 8,388,630 B2 | Page 1 of 1 |
| APPLICATION NO. | : 10/942105 | |
| DATED | : March 5, 2013 | |
| INVENTOR(S) | : James A. Teague et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 817 days.

Signed and Sealed this

Second Day of December, 2014

Michelle K. Lee
*Deputy Director of the United States Patent and Trademark Office*